(12) United States Patent
Tisdell et al.

(10) Patent No.: US 6,413,992 B1
(45) Date of Patent: Jul. 2, 2002

(54) 3-(SUBSTITUTED PYRIDYL)-1,2,4-TRIAZOLE COMPOUNDS

(75) Inventors: Francis E. Tisdell, Carmel; Peter L. Johnson; James T. Pechacek, both of Indianapolis; Scott J. Bis; Vidyadhar B. Hegde, both of Carmel; Joe R. Schoonover, Jr., Brownsburg; Leonard P. Dintenfass, Indianapolis; James M. Gifford, Lebanon; Donald H. DeVries, Fishers; Timothy P. Martin, Indianapolis, all of IN (US); Perry V. Ripa, Sun Prairie, WI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/425,091

(22) Filed: Oct. 22, 1999

Related U.S. Application Data

(60) Provisional application No. 60/105,356, filed on Oct. 23, 1998.

(51) Int. Cl.⁷ ................. A01N 43/653; C07D 401/04
(52) U.S. Cl. ..................... 514/340; 546/272.4
(58) Field of Search ................ 514/341; 546/272.4

(56) References Cited

U.S. PATENT DOCUMENTS

| | | | | |
|---|---|---|---|---|
| 3,862,954 A | * | 1/1975 | Omodei-Sale | 260/296 R |
| 3,963,731 A | * | 6/1976 | Novello et al. | 260/294.8 F |
| 3,984,558 A | * | 10/1976 | Baldwin et al. | 424/263 |
| 4,011,218 A | * | 3/1977 | Baldwin et al. | 260/250 AH |
| 4,018,793 A | * | 4/1977 | Stoss et al. | 260/330.5 |
| 4,713,383 A | * | 12/1987 | Francis et al. | 514/267 |
| 4,788,210 A | * | 11/1988 | Luthy et al. | 514/383 |
| 5,284,860 A | * | 2/1994 | Ozaki et al. | 514/340 |
| 5,380,944 A | * | 1/1995 | Ozaki et al. | 564/81 |
| 6,015,826 A | * | 1/2000 | Pechacek et al. | 514/383 |

FOREIGN PATENT DOCUMENTS

| | | | |
|---|---|---|---|
| AU | 646990 | * | 4/1991 |
| EP | 217552 | * | 4/1987 |
| EP | 559363 | * | 9/1993 |
| FR | 1238943 | * | 12/1960 |

* cited by examiner

*Primary Examiner*—Patricia L. Morris
(74) *Attorney, Agent, or Firm*—Donald R. Stuart; Craig E. Mixan

(57) ABSTRACT

Compounds of the formula

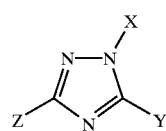

(1)

wherein one of X and Y is lower alkyl, haloalkyl, lower alkenyl, lower alkynyl, or alkoxyalkyl; and the other of X and Y is optionally substituted phenyl, pyridyl, thienyl, cyclopropyl, or thiazolyl; and Z is subtituted pyridyl are useful as insecticides and acaricides. New synthetic procedures and intermediates for preparing the compounds, pesticide compositions containing the compounds, and methods of controlling insects and mites using the compounds are also provided.

9 Claims, No Drawings

3-(SUBSTITUTED PYRIDYL)-1,2,4-TRIAZOLE COMPOUNDS

RELATED APPLICATION

This application claims priority from U.S. Provisional Patent Application Ser. No. 60/105,356, filed Oct. 23, 1998.

FIELD OF THE INVENTION

This invention provides new compounds that are useful as insecticides and acaricides, new synthetic procedures and intermediates for preparing the compounds, pesticide compositions containing the compounds, and methods of controlling insects and mites using the compounds.

BACKGROUND OF THE INVENTION

There is an acute need for new insecticides and acaricides. Insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore a need exists for new insecticides and acaricides, and particularly for compounds that have new or atypical modes of action.

A number of 3,5-diphenyl-1H-1,2,4-triazole derivatives have been described in the literature as having acaricidal activity. U.S. Pat. No. 5,482,951; JP 8092224, EP572142, JP 08283261. To applicants knowledge, however, none of these compounds has become a commercial product. Nitro furanyl triazoles are described by L. E. Benjamin and H. R. Snyder as antimicrobials (*J. Heterocyclic Chem.* 1976, 13, 1115) and by others as antibacterials (*J. Med. Chem.* 1973, 16(4), 312–319; *J. Med. Chem.* 1974, 17(7), 756–758). The present invention provides novel compounds with commercial level activity against mites and insects.

SUMMARY OF THE INVENTION

This invention provides novel substituted pyridyl triazole derivatives especially useful for the control of insects and mites.

More specifically, the invention provides novel insecticidally active compounds of the formula (1)

$$\text{(1)}$$

wherein

Z is pyridyl, optionally substituted with up to four groups independently selected from the group consisting of Cl, F, methyl, halomethyl, methoxy, halomethoxy, and methylthio;

one of X and Y is H, lower alkyl, haloalkyl, lower alkenyl, lower alkynyl, alkoxyalkyl, phenyl, or substituted phenyl;

the other of X and Y is a group selected from wherein $R^2$ is halo, lower alkyl, haloalkyl, lower alkenyl, lower alkynyl, or alkoxyalkyl;

$R^3$ is selected from H, halo, lower alkyl, $(C_7-C_{21})$ straight chain alkyl, hydroxy, lower alkoxy, haloalkyl, haloalkoxy, alkoxyalkyl, alkoxyalkoxy, lower alkenyl, haloalkenyl, CN, $NO_2$, $CO_2R^6$, CON$(R^6)_2$, $(C_3-C_6)$ cycloalkyl, $S(O)_mR^6$, SCN, pyridyl, pyridyloxy, substituted pyridyl, substituted pyridyloxy, phenoxy, substituted phenoxy, isoxazolyl, substituted isoxazolyl, naphthyl, substituted naphthyl, phenyl, substituted phenyl, $-(CH_2)_nR^6$, $-CH=CHR^6$, $-C\equiv CR^6$, $-CH_2OR^6$, $-CH_2SR^6$, $-CH_2NR^6R^6$, $-OCH_2R^6$, $-SCH_2R^6$, $-NR^6CH_2R^6$, $-NCH_3NH_2$, $R^4$ and $R^5$ are independently H, halo, lower alkyl, lower alkoxy, haloalkyl, haloalkoxy, CN, $NO_2$, $CO_2R^6$, CON$(R^6)_2$, or $S(O)_m$ alkyl, or $R^4$ and $R^5$ form a 5 or 6 member saturated or unsaturated carbocyclic ring which may be substituted by 1 or 2 halo, lower alkyl, lower alkoxy or haloalkyl groups;

$R^6$ is H, lower alkyl, haloalkyl, lower alkenyl, lower alkynyl, phenyl, or substituted phenyl;

m is 0, 1, or 2; and n is 1 or 2;

p is an integer from 2 to 6;

or a phytologically acceptable acid addition salt or N-oxide thereof.

The priority document described compounds of the formula

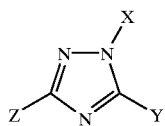

wherein
Z is 2-pyridyl, 3-pyridyl, or 4-pyridyl, optionally substituted with up to four groups independently selected from the group consisting of Cl, F, methyl, halomethyl, methoxy, and halomethoxy;
X is lower alkyl, haloalkyl, lower alkenyl, lower alkynyl, or alkoxyalkyl;
Y is a group selected from

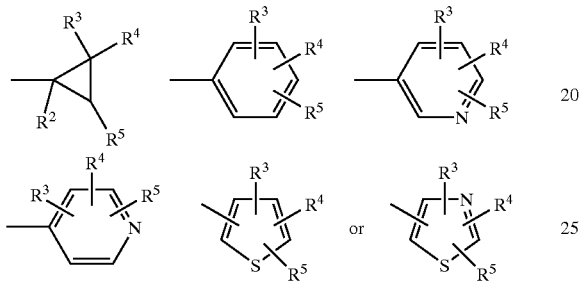

wherein
R is lower alkyl, haloalkyl, lower alkenyl, lower alkynyl, or alkoxyalkyl;
R is selected from H, halo, lower alkyl, ($C_7$–$C_{21}$) straight chain alkyl, hydroxy, lower alkoxy, haloalkyl, haloalkoxy, alkoxyalkyl, alkoxyalkoxy, lower alkenyl, haloalkenyl, CN, $NO_2$, $CO_2R^6$, CON($R^6$)$_2$, ($C_3$–$C_6$) cycloalkyl, $S(O)_mR^6$, SCN, pyridyl, substituted pyridyl, isoxazolyl, substituted isoxazolyl, naphthyl, substituted naphthyl, phenyl, substituted phenyl, —($CH_2$)$_n$$R^6$, —CH=$CHR^6$, —C≡$CR^6$, —$CH_2OR^6$, —$CH_2SR^6$, —$CH_2NR^6R^6$, —$OCH_2R^6$, —$SCH_2R^6$, —$NR^6CH_2R^6$,

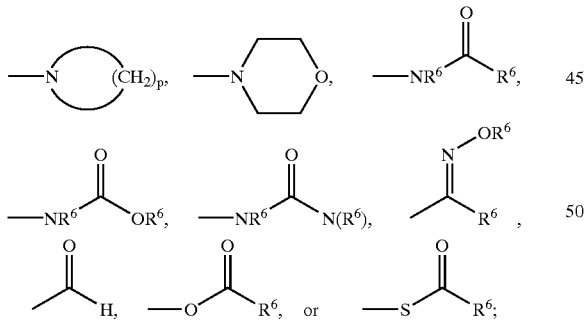

$R^4$ and $R^5$ are independently H, halo, lower alkyl, lower alkoxy, haloalkyl, haloalkoxy, CN, $CO_2R^6$, CON($R^6$)$_2$, or $S(O)_m$ alkyl, or
$R^4$ and $R^5$ form a 5 or 6 member saturated or unsaturated carbocyclic ring which may be substituted by 1 or 2 halo, lower alkyl, lower alkoxy or haloalkyl groups;
$R^6$ is H, lower alkyl, haloalkyl, lower alkenyl, lower alkynyl, phenyl, or substituted phenyl;
m is 0, 1, or 2; and
n is 1 or 2;
p is an integer from 2 to 6;

or a phytologically acceptable acid addition salt or N-oxide thereof.

Preferred compounds of formula (1) include the following classes:

(1) Compounds of formula (1) wherein wherein one of X and Y is lower alkyl, haloalkyl, lower alkenyl, lower alkynyl, substituted phenyl, or alkoxyalkyl; and the other of X and Y is optionally substituted phenyl, pyridyl, thienyl, cyclopropyl, or thiazolyl;

(2) Compounds of formula (1) wherein Z is a 4-pyridyl group optionally substituted with up to four groups independently selected from Cl, F, methyl, halomethyl, methylthio, methoxy, and halomethoxy.

(3) Compounds of class (2) wherein Z is a 4-pyridyl group of the formula

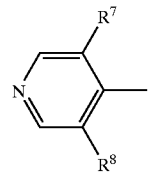

wherein $R^7$ and $R^8$ are independently H, Cl, F, methyl, halomethyl, methoxy, or halomethoxy.

(4) Compounds of class (3) wherein $R^7$ and $R^8$ are independently methyl, F or Cl.

(5) Compounds of class (4) wherein $R^7$ and $R^8$ are both F, where $R^7$ is chloro and $R^8$ is methyl, or where $R^7$ is fluoro and $R^8$ is methyl.

(6) Compounds of class (4) wherein $R^7$ and $R^8$ are both Cl.

(7) Compounds of formula (1), and particularly compounds of class (1), (2), (3), (4), (5), or (6) as defined above, wherein Y is a group of the formula

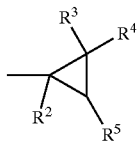

where $R^2$, $R^3$, $R^4$, and $R^5$ are as defined in formula (1)

(8) Compounds of formula (1), and particularly compounds of class (1), (2), (3), (4), (5), or (6) as defined above, wherein Y is a group of the formula

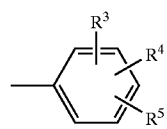

where $R^3$, $R^4$, and $R^5$ are as defined in formula (1).

(9) Compounds of class (7) wherein Y is a group of the formula

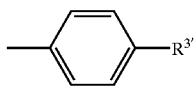

where $R^3$ is an electron withdrawing group such as Cl, Br, $CF_3$ or $NO_2$.

(10) Compounds of formula (1), and particularly compounds of class (1), (2), (3), (4), (5), or (6) as defined above, wherein Y is a group of the formula

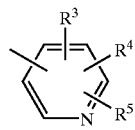

where $R^3$, $R^4$, and $R^5$ are as defined in formula (1).

(11) Compounds of formula (1), and particularly compounds of class (1), (2), (3), (4), (5), or (6) as defined above, wherein Y is a group of the formula

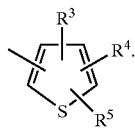

where $R^3$, $R^4$, and $R^5$ are as defined in formula (1).

(12) Compounds of class (11) wherein $R^3$, $R^4$, and $R^5$ are independently selected from H, halo, alkyl, and alkoxy.

(13) Compounds of class (12) wherein $R^3$, $R^4$, and $R^5$ are independently selected from H, alkyl, and halo.

(14) Compounds of class (13) wherein $R^3$, $R^4$, and $R^5$ are independently selected from H, methyl, Cl, and Br.

(15) Compounds of formula (1), and particularly compounds of class (1), (2), (3), (4), (5), or (6) as defined above, wherein Y is a group of the formula

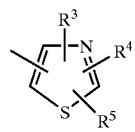

where $R^3$, $R^4$, and $R^5$ are as defined in formula (1).

(16) Compounds of formula (1) or any one of classes (1) through (15) wherein X is methyl.

The invention also provides new processes and intermediates for preparing compounds of formula (1) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

The term "lower alkyl" refers to ($C_1$–$C_6$) straight hydrocarbon chains and ($C_3$–$C_6$) branched and cyclic hydrocarbon groups.

The terms "lower alkenyl" and "lower alkynyl" refer to ($C_2$–$C_6$) straight hydrocarbon chains and ($C_3$–$C_6$) branched hydrocarbon groups containing at least one double or triple bond, respectively.

The term "lower alkoxy" refers to —O-lower alkyl.

The terms "halomethyl", "haloalkyl", and "haloalkenyl" refer to methyl, lower alkyl, and lower alkenyl groups substituted with one or more halo atoms.

The terms "halomethoxy" and "haloalkoxy" refer to methoxy and lower alkoxy groups substituted with one or more halo atoms.

The term "alkoxyalkyl" refers to a lower alkyl group substituted with a lower alkoxy group.

The term "alkoxyalkoxy" refers to a lower alkoxy group substituted with a lower alkoxy group.

The terms "substituted naphthyl", "substituted thienyl," "substituted pyrimidyl," "substituted pyrazolyl," "substituted pyridyl," and "substituted isoxaxolyl" refer to the ring system substituted with one or more groups independently selected from halo, halo ($C_1$–$C_4$) alkyl, CN, $NO_2$, ($C_1$–$C_4$) alkyl, ($C_3$–$C_4$) branched alkyl, phenyl, ($C_1$–$C_4$) alkoxy, or halo ($C_1$–$C_4$) alkoxy.

The term "substituted phenyl" refers to a phenyl group substituted with one or more groups independently selected from halo, ($C_1$–$C_{10}$) alkyl, branched ($C_3$–$C_6$) alkyl, halo ($C_1$–$C_7$) alkyl, hydroxy ($C_1$–$C_7$) alkyl, ($C_1$–$C_7$) alkoxy, halo ($C_1$–$C_7$) alkoxy, phenoxy, phenyl, $NO_2$, OH, CN, ($C_1$–$C_4$) alkanoyl, benzoyl, ($C_1$–$C_4$) alkanoyloxy, ($C_1$–$C_4$) alkoxycarbonyl, phenoxycarbonyl, or benzoyloxy.

The term "pyridyl" refers to a 2-pyridyl, 3-pyridyl, or 4-pyridyl group.

Unless otherwise indicated, when it is stated that a group may be substituted with one or more substituents selected from an identified class, it is intended that the substituents may be independently selected from the class.

Synthesis

Compounds of formula (1) can be prepared by the methods described in U.S. Pat. Nos. 5,380,944 and 5,284,860 (Production Methods 1, 2 and 3). Additional methods will be described hereinafter.

Compounds of formula (1) wherein X is H, lower alkyl, haloalkyl, lower alkenyl, lower alkynyl, alkoxyalkyl, phenyl, or substituted phenyl; and Y is a group selected from

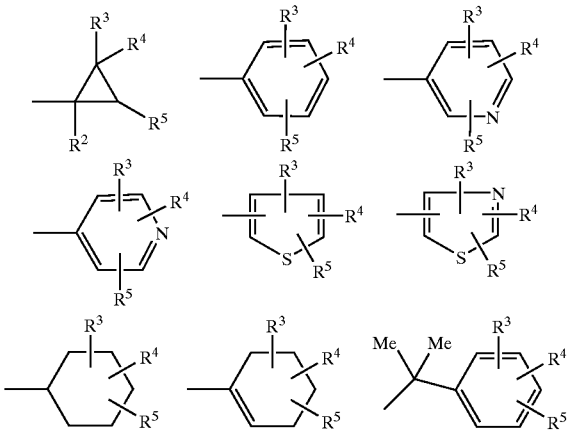

can be prepared by the method illustrated in Scheme I:

Scheme I

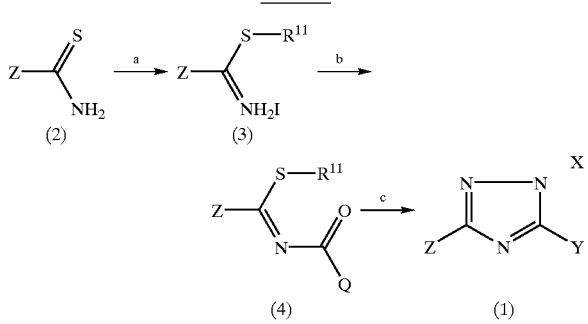

wherein X, Y and Z are as defined in formula (1) and $R^{11}$ is lower alkyl, preferably methyl.

The starting material of formula (2) used in Scheme I can be prepared by reacting a amide of formula Z—$CONH_2$ with phosphorus pentasulfide in pyridine at reflux.

In step a of Scheme I the compound of formula (2) is reacted with lower alkyl iodide, e.g. iodomethane, in acetone to provide a compound of formula (3). Acetone is the preferred solvent, however other polar aprotic solvents such as DMF or THF can be used.

In step b of Scheme I the compound of formula (3) is reacted with an acid chloride of formula Y—COCl in a nonreactive organic solvent such as benzene, toluene, xylenes, chloroform, dichloromethane, or 1,2-dichloroethane, at a temperature in the range from 0° C. to the boiling point of the solvent.

In step c of Scheme I, the N-acylimidate of formula (4) is reacted with an N-methylhydrazine to provide the product of formula (1). The reaction is carried out in benzene, toluene, xylenes, chloroform, dichloromethane, or 1,2-dichloroethane, at a temperature in the range from 0° C. to the boiling point of the solvent.

In another of its aspects, the invention provides novel intermediates of the formulas (2), (3), and (4) as defined above.

EXAMPLE 1

S-methylthio-3,5-dichloro-4-pyridylimidinium iodide

A. Preparation of 3,5-dichloro-4-pyridinethioamide

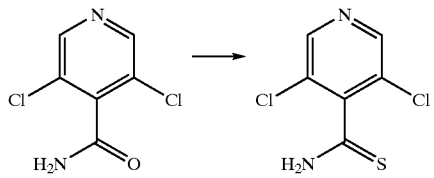

Into a 3000-mL three-necked round bottom flask equipped with a condenser, mechanical stirrer under an atmosphere of nitrogen was added pyridine (1500 mL), then 3,5-dichloro-4-pyridine-carboxamide (92.9 g., 0.486 mole) (which dissolved), and tetraphosphorus decasulfide (237 g., 0.535 moles)(which had almost dissolved then a bright yellow precipitate formed and an exotherm heated the mixture to 60° C.). The slurry was allowed to stir for 1 hr (temperature had dropped to 45° C.) and then the temperature was then raised and when it reached 100° C. all of the solids had dissolved and continued heating to 118° C. and was maintained at 115° C. for 4 hr. The mixture was poured into water (3750 mL) carefully as gas began to evolve and the temperature of the aqueous solution rose to approximately 45° C. and was allowed to sit at room temperature over two nights. To the resulting mixture was added water (6000 mL) and was extracted with methylene chloride (3×2000 mL), washed with water (3×1000 mL) and the solvent removed in vacuo to give a brownish yellow liquid, with much pyridine present. The vacuum pump was connected to the rotary evaporator to remove the residual pyridine. The residue (brown solid) was triturated with diethyl ether (3×1500 mL), treated with decolorizing carbon and the solvent removed in vacuo to give a solid which contained pyridine. The yellow solid was slurried in water (2×200 mL) and dried in vacuo at 60° C. to give 63.2 g of a light yellow solid (62.8% yield): mp 186–187° C.; TLC [50/50 ethyl acetate/hexanes] showed amide at Rf=0.31 and thioamide Rf=0.53; $^1$H NMR (DMSO-$d_6$) d 10.6 (s, b, 1H), 10.0 (s, b, 1H), 8.6 (s, 2H).

B. The following step illustrates the preparation of the S-methyl imidate of formula (3a)

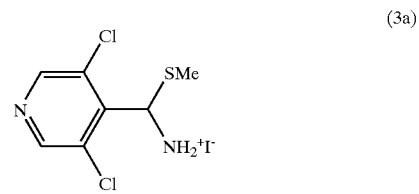

Into a 3 L three necked flask equipped with a magnetic stirrer was added acetone (80 mL) and 3,5-dichloro-4-pyridylthioamide (15.87 g, 76.6 mmol). To the stirred solution iodomethane (10.89 g, 4.77 mL, 76.6 mmol) was added dropwise. The slurry was stirred over night. The resulting yellow solids were removed via filtration and washed with ether to obtain 15.23 grams (57%) of S-methylthio-3,5-dichloro-4-pyridylimidinium iodide: mp 158–161° C. $^1$H NMR (DMSO-$d_6$) d 8.8 (s, 2H), 7.8 (sb, 2H), 2.6 (s, 3H).

EXAMPLE 2

N-(2,4-dichlorobenzoyl)-S-methylthio-3,5-dichloro-4-pyridylimidate

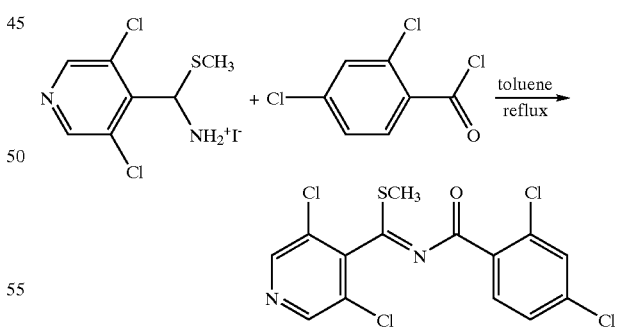

To mixture of 2,4-dichlorobenzoyl chloride (0.94 g, 4.5 mmol) in 50 ml of dry toluene was added triethylamine (1.8 g, 18 mmol) and S-methylthio-3,5-dichloro-4-pyridylimidinium iodide (1.58 g, 4.5 mmol). The mixture was stirred at room temperature for two hours and then refluxed for two hours. The mixture was partitioned between brine and ether. The organic phase was dried ($MgSO_4$), the solvent evaporated, and the residue was chromatographed on silica gel using ethyl acetate/hexane as the eluant; 20:80.

The product fractions were collected and evaporated to give 1.40 g (79% yield) of the title product as a reddish solid. Recrystallization afforded the title product (1.01 g., 57% yield) as a reddish solid. mp 104–105° C. $^1$H NMR d 8.51 (s, 2H), 7.86–7.89 (d, 1H), 7.45 (s, 1H) 7.28–7.31 (m, 1H), 2.65 (s, 3H). Calculated for $C_{14}H_8Cl_4N_2SO$: C, 42.66; H, 2.05; N, 7.11; Found: C, 42.47; H, 1.96; N, 6.93.

EXAMPLE 3

3-(3,5 dichloro-4-pyridyl)-5-(2,4-dichlorobenzyl)-1-methyl[1,2,4]triazole

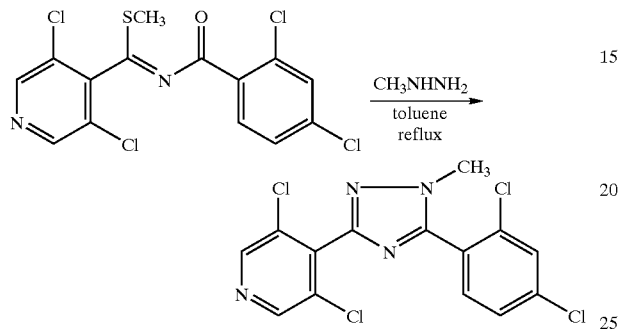

A solution of 0.678 g (1.72 mmol) of the N-acyl-S-methylthioimidate of Example 2 and 0.317 g (6.88 mmol) of methylhydrazine in 20 ml of toluene was refluxed four hours and then stirred overnight at ambient temperature. The solvent removed in vacuo and the residue was chromatographed on silica gel using ethyl acetate/hexane as the eluant; 25:75. The product fractions were collected and evaporated to give 0.31 g (48% yield) of the title product as white crystals. mp 79–81° C. $^1$H NMR d 8.6 (s,2 H), 7.6 (s, 1H), 7.51–7.54 (d, 1H) 7.42–7.46 (m, 1H), 3.91 (s, 3H). Calculated for $C_{14}H_8Cl_4N_4$: C, 44.96; H, 2.16; N, 14.98; Found: C, 44.89; H, 2.10; N, 14.81.

EXAMPLE 4

N-isonicotinoyl-S-methylthio-3,5-dichloro-4-pyridylimidate

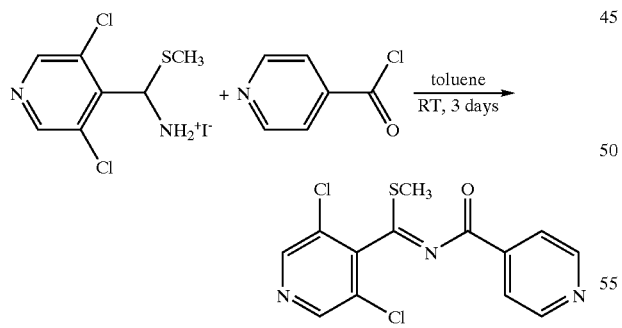

To a mixture of isonicotinoyl chloride (1.14 g, 8.12 mmol) in 40 mL of dry toluene was added triethylamine (3.28 g, 32.5 mmol.) and S-methylthio-3,5-dichloropyridylimidinium iodide (2.83 g, 8.12 mmol). The mixture was stirred at room temperature for 72 hours. The mixture was partitioned between brine and ether. The organic phase was dried ($MgSO_4$), the solvent evaporated, and the residue was chromatographed on silica gel using ethyl acetate/hexane as the eluant; 50:50. The product fractions were collected and evaporated to give 0.88 g (33% yield) of the title product as tan solid. mp 122–123° C. $^1$H NMR d 8.79–8.81 (d, 2H), 8.52 (s, 2H), 7.82–7.84 (d, 2H), 2.69 (s, 3H); Calculated for $C_{13}H_9Cl_2N_3SO$: C, 47.89; H, 2.79; N, 12.88; Found: C, 47.74; H, 2.69; N, 12.63.

EXAMPLE 5

3-(3,5 dichloro-4-pyridyl)-5-isonicotinyl-1-methyl[1,2,4]triazole

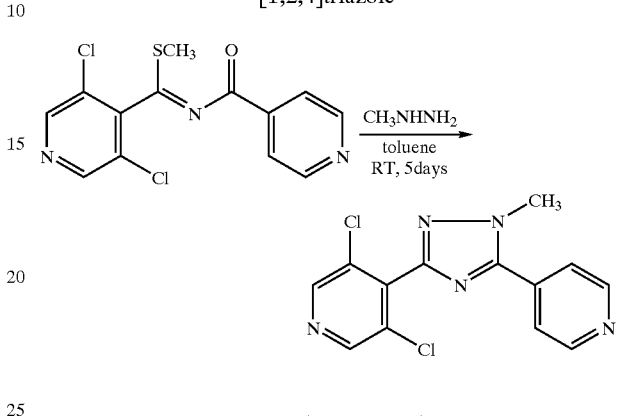

A solution of 0.55 g (1.69 mmol) of the N-acyl-S-methylthioimidate of Example 4 and 0.155 g (3.37 mmol) of methylhydrazine in 10 ml of toluene was stirred 5 days at ambient temperature. The solvent was removed in vacuo and the residue was chromatographed on silica gel using ethyl acetate as the eluant. The product fractions were collected and evaporated to give 0.222 g (43% yield) of the title product as white crystals. mp 130–132° C. $^1$H NMR d 8.84–8.86 (d,2 H), 8.64 (s, 2H), 7.72–7.74 (d, 2H), 4.20 (s, 3H). Calculated for $C_{13}H_9Cl_2N_5$: C, 51.00; H, 2.97; N, 22.88; Found: C, 50.55; H, 3.04; N, 22.08.

EXAMPLE 6

3-(3,5 dichloro-4-pyridyl)-5-(2,2-dichloro-1-methyl cyclopropyl)-1-methyl[1,2,4]triazole

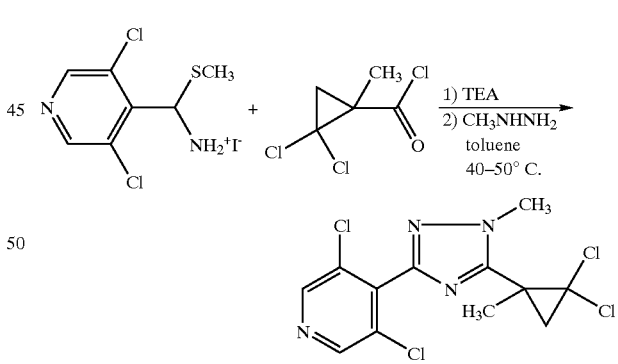

To a solution of S-methylthio-3,5-dichloropyridylimidinium iodide (0.585 g, 1.67 mmol) and triethylamine (0.675 g, 6.68 mmol.) in 15 mL of dry toluene was added a solution of 2,2-dichloro-1-methyl-cyclopropanoyl chloride (0.337 g, 1.8 mmol) in 10 ml toluene. The mixture was refluxed three hours. A solution of methylhydrazine (0.317 g , 6.88 mmol) in 10 mL of toluene was added dropwise and the mixture refluxed one hour and then stirred overnight at ambient temperature. The solvent removed in vacuo and the residue was chromatographed on silica gel using ethyl acetate/hexane as the eluant; 25:75.

The product fractions were collected and evaporated to give 79 mg (13% yield) of the title product as yellow solid. mp 79–83° C.

EXAMPLE 7

N-(3-Methyl-2-thienoyl)-S-methylthio-3,5-dichloro-4-pyridylimidate

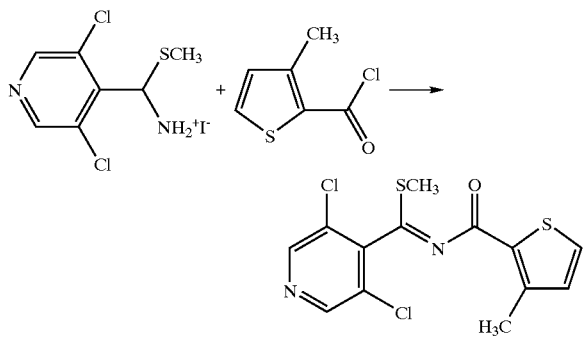

Pyridine (0.51 ml, 6.3 mmol) was added dropwise to a slurry of 3-methyl-2-thiophenecarbonyl chloride (0.48 g, 3.0 mmol) and S-methylthio-3,5-dichloropyridylimidinium iodide (1.05 g, 3.0 mmol) in 5 mL of 1,2-dichloroethane, under $N_2$, at room temperature. After stirring at room temperature for 60 minutes the reaction mixture was poured into $H_2O$ (25 ml) and extracted with ethyl acetate (3×25 ml). The combined organic extracts were washed with $H_2O$ (1×25 ml), saturated sodium chloride (1×25 ml), dried over anhydrous $MgSO_4$, filtered and concentrated in vacuo to give 0.99 g of a yellow oil. This was chromatographed over silica gel (MPLC), eluting with 90% hexane/10% ethyl acetate. Isolation of the major product gave 0.827 g (80% yield) of the title compound as a faint yellow solid: mp 99–101° C. $^1H$ NMR $CDCl_3$ d 8.51 (s, 2H), 7.45 (d, 1H), 6.94 (d, 1H), 2.64 (s, 3H), 2.49 (s, 3H).

EXAMPLE 8

1-Methyl-3-(3,5-dichloro-4-pyridyl)-5-(3-methyl-2-thienyl)[1,2,4]triazole

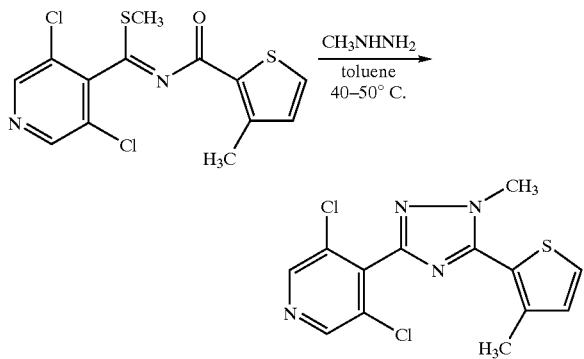

Methylhydrazine (0.225 ml, 4.2 mmol) was added dropwise to a solution of the N-acyl-S-methylthioimidate of Example 7 (0.725 g, 2.1 mmol) in 5 ml of toluene, under $N_2$, at room temperature. After stirring at room temperature for 24 hours, TLC analysis showed a 2:1 mixture of starting material to product. An additional 0.2 ml of methylhydrazine was added and the mixture warmed to 40° C. After 5 hours TLC shows a 1:1 mixture of starting material to product. An additional 0.2 ml of methylhydrazine was added and stirring continued for 24 hours at 40–50° C. at which time TLC analysis indicated that all of the starting material had been consumed. The reaction mixture was concentrated in vacuo and the resultant yellow oil was chromatographed over silica gel (MPLC), eluting with 80% hexane/20% ethyl acetate. Isolation of the major product gave 0.422 g (65% yield) of the title compound as a faint yellow oil. $^1H$ NMR $CDCl_3$ 8.61(s, 2H), 7.47(d, 1H), 7.02(d, 1H), 4.05(s, 3H), 2.40(s, 3H).

EXAMPLE 9

N-3-pyridoyl-S-methylthio-3,5-dichloro-4-pyridylimidate

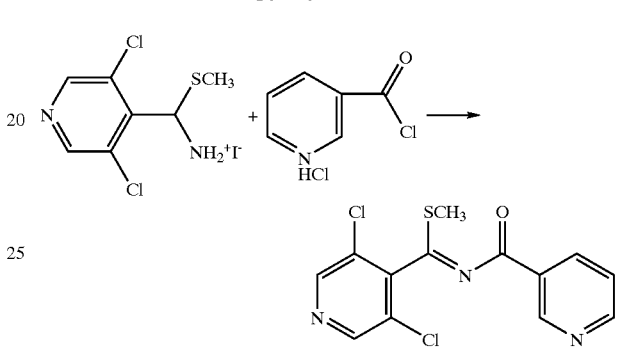

Pyridine (0.78 ml, 9.6 mmol) was added dropwise to a mixture of S-methylthio-3,5-dichloropyridylimidinium iodide (1.05 g, 3.0 mmol) and nicotinyl chloride hydrochloride (0.53 g, 3.0 mmol) in 5 ml of 1,2-dichloroethane, under $N_2$, at room temperature. After 90 minutes at room temperature the reaction mixture was poured into $H_2O$ (25 ml) and extracted with ethyl acetate (3×25 ml). The combined organic extracts were washed with $H_2O$ (1×25 ml), saturated sodium chloride (1×25 ml), dried over anhydrous $Na_2SO_4$, filtered and concentrated in vacuo to give 0.76 g of a brown oil. This was chromatographed on silica gel (MPLC) eluting with 70% hexane/30% ethyl acetate. Isolation of the major product gave 0.714 g (73% yield) of the desired product as a yellow oil which slowly solidified: mp 106–108° C. $^1H$ NMR $CDCl_3$ 9.27 (d, 1H), 8.78 (dd, 1H), 8.51 (s, 2H), 8.28 (m, 1H) 7.40 (m, 1H), 2.68 (s, 3H).

EXAMPLE 10

1-Methyl-3-(3,5-dichloro-4-pyridyl)-5-(3-pyridyl)[1,2,4]triazole

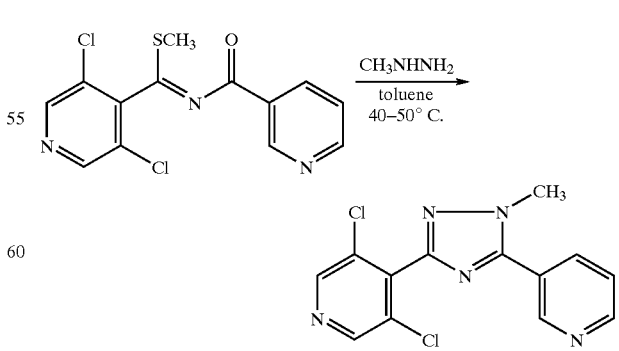

Methylhydrazine (0.20 ml, 3.8 mmol) was added to a solution of the N-acyl-S-methylthioimidate of Example 9

(0.606 g, 1.9 mmol) in 5 ml of toluene, under $N_2$, at room temperature. The resultant mixture was warmed to ~50° C. After stirring at 60–70° C. for five hours TLC analysis showed only a trace amount of the starting material present. The reaction mixture was concentrated in vacuo. The residual yellow oil was chromatographed on silica gel (MPLC), eluting with 50% hexane/50% ethyl acetate. Isolation of the major product gave 0.291 g (50% yield) of the desired product as a yellow oil. 1H NMR $CDCl_3$ 9.05 (d, 1H), 8.80 (dd, 1H), 8.63 (s, 2H), 8.14 (m, 1H), 7.51 (m, 1H), 4.17 (s, 3H).

EXAMPLE 11

1-Methyl-3-(3,5-dichloro-4-pyridyl)-5-(3-pyridyl-N-oxide)[1,2,4]triazole

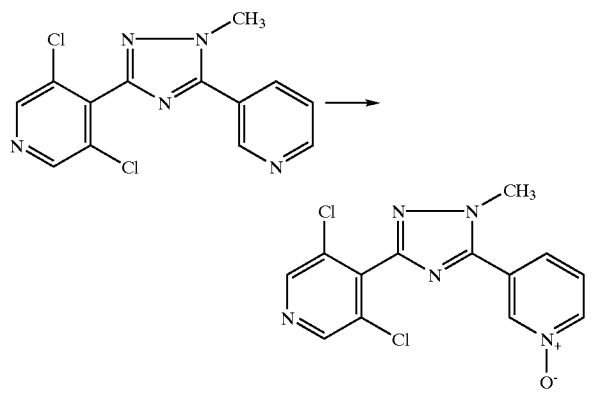

A solution of the pyridine derivative of Example 10 (0.150 g, 0.5 mmol) in 2 ml of dichloromethane was treated in one portion with m-chloroperoxybenzoic acid (0.173 g, ~0.55 mmol, 50–60%), while cooling in an ice bath. The resultant mixture was gradually allowed to warm to room temperature. After five hours at room temperature TLC analysis indicated that all of the starting material had been consumed. The reaction mixture was diluted with dichloromethane (25 ml), washed with 2N NaOH (2×10 ml) and saturated sodium chloride (1×10 ml). The organic phase was dried over anhydrous $MgSO_4$, filtered and concentrated in vacuo to give 0.105 g (65% yield ) of the desired product as a light yellow foam. $^1H$ NMR CDCl3 8.63 (d, 3H), 8.35 (m, 1H), 7.70 (d, 1H), 7.47 (t, 1H), 4.18 (s,3H).

EXAMPLE 12

1-Methyl-3-(3,5-dichloro-4-pyridyl)-5-(6-chloro-3-pyridyl)[1,2,4]triazole

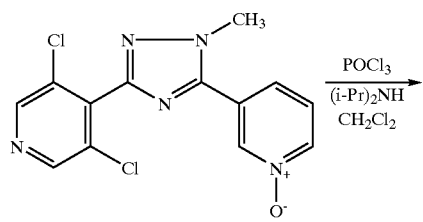

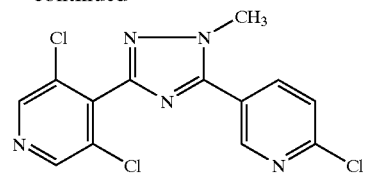

Phosphorus oxychloride (48 ml, 0.52 mmol) and diisopropylamine (73 ml, 0.52 mmol) were added simultaneously, via syringe, to a solution of the pyridine-N-oxide of Example 11 (83 mg, 0.26 mmol) in 2 ml of dichloromethane, under $N_2$, at room temperature. After two hours TLC analysis showed much starting material still present and two minor products. The reaction mixture was concentrated in vacuo and the residue taken up in $POCl_3$ (2 ml) and heated to reflux. After two hours it appeared that all of the starting material had been consumed. The reaction mixture was cautiously poured into 2N NaOH (10 ml) and extracted with $CH_2Cl_2$ (3×10 mL). The combined organic extracts were washed with saturated sodium chloride (1×10 ml), dried over anhydrous $MgSO_4$, filtered and concentrated in vacuo to give 45 mg of a yellow oil. This was chromatographed on silica gel (MPLC), eluting with 60% hexane/40% ethyl acetate. Isolation of the major product gave 17 mg (19% yield) of the desired product as a yellow oil. $^1H$ NMR $CDCl_3$ 8.83 (d, 1H), 8.64 (sb, 2H), 8.11–8.14 (dd, 1H), 7.53–7.56 (d, 1H), 4.16 (s, 3H).

EXAMPLE 13

3-(3,5 dichloro-4-pyridyl N-oxide)-5-(4-chlorophenyl)-1-methyl[1,2,4]triazole

A solution of 0.378 g (1.12 mmol) of 3-(3,5 dichloro-4-pyridyl)-5-(4-chlorophenyl)-1-methyl[1,2,4]triazole and 0.414 g (1.2 mmol) of meta-chloroperbenzoic acid in 12 ml of methylene chloride was stirred 3 days at ambient temperature. The solvent removed in vacuo and the residue was chromatographed on silica gel using ethyl acetate as the eluant. The product fractions were collected and evaporated to give 0.33 g (83% yield) of the title product as a yellow solid. mp 161–166° C. $^1H$ NMR d 8.28 (s,2 H), 7.71–7.74 (d, 2H), 7.53–7.56 (d, 2H), 4.12 (s, 3H).

EXAMPLE 14

Preparation of N-p-chlorobenzoyl-3,5-dichloropyridin-4-yl methyl thioimidate

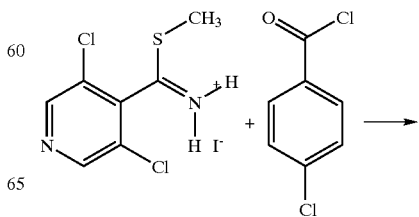

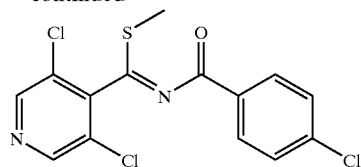

Into a 1000 mL three necked round bottom flask equipped with a mechanical stirrer, thermometer and condenser under an atmosphere of nitrogen was added methyl 3,5-dichloropyridin-4-yl thioimidate (63.4 g, 0.163 mol, 90% pure), 1,2-dichloroethane (327 mL) and pyridine (25.8 g, 26.3 mL, 0.326 mol). The temperature of the stirred mixture was raised to 45° C. and dropwise was added p-chlorobenzoyl chloride (28.6 g, 20.8 mL, 0.163 mol) over a 20-min period. An exotherm raised the temperature to 66° C. and the slurry was allowed to stir at that temperature for 0.5 h. The slurry was cooled to room temperature and the solids removed via filtration and washed with a small portion of EDC. An equal volume of methylene chloride was added to the filtrate which was then washed with dilute acid (2×200 mL), saturated sodium bicarbonate, brine, dried ($Na_2SO_4$), and the solvent removed in vacuo to give 67 g. The crude material was put through a plug (670 g) of silica gel eluting with methylene chloride which removed all of the polar material which stayed at the origin and removed the non-polar by taking appropriate fractions. Total clean product of 48.2 g (81.8% yield) as yellow crystalline material: mp 121–122° C.; $^1$H NMR ($CDCl_3$) δ8.5 (s, 2H), 8.0 (d, J=8.7 Hz, 2H), 7.4 (d, J=8.7 Hz, 2H), 2.6 (s, 3H). Anal. Calcd. for $C_{14}H_9Cl_3N_2O$: C, 46.75; H, 2.52; N, 7.79. Found: C, 46.75; H, 2.51; N, 7.67.

EXAMPLE 15

Preparation of 3-(3,5-dichloro-4-pyridyl)-5-(4-chlorobenzyl)-1-methyl[1,2,4]triazole

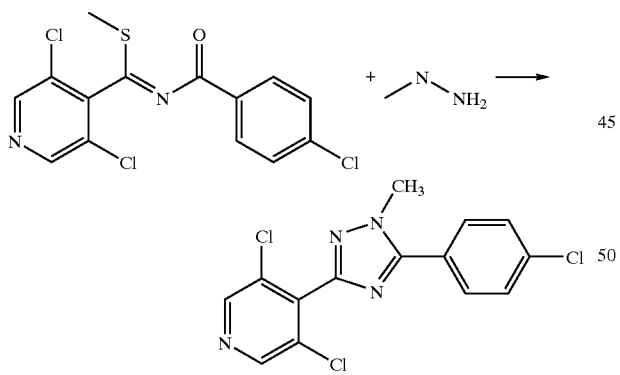

Into a 2000 mL three necked round bottom flask equipped with a mechanical stirrer and condenser under an atmosphere of nitrogen was added toluene (646 mL), N-p-chlorobenzoyl methyl (3,5-dichloropyridin-4-yl)thioimidate (64.6 g, 0.179 mol), and methyl hydrazine (41.4 g, 47.8 mL, 0.898 mol). The resulting mixture was allowed to reflux for 1 h and the temperature rose to 92° C. The solvent was removed in vacuo and the residual yellow solids were dissolved in methylene chloride (1000 mL), washed with water (2×200 mL), brine (200 mL), and the solvent removed in vacuo to give an oil which crystallized on standing. The solids were dissolved in refluxing absolute ethanol (200 mL) and the hot solution seeded with an authentic sample of the title compound. The resulting solids were removed via filtration and dried in vacuo at 70° C. to give 31.6 g (52% yield) of the title compound: mp 142–143° C.; 98.9% pure by GC analysis.

$^1$H NMR ($CDCl_3$) δ8.6 (s, 2H), 7.7 (d, J=8.4 Hz, 2H), 7.5 (d, J=8.4 Hz, 2H), 4.1 (s, 3H).

Examples 16–19 illustrate preparation of compounds of formula (1) wherein Y is H, lower alkyl, haloalkyl, lower alkenyl, lower alkynyl, alkoxyalkyl, phenyl, or substituted phenyl; and X is a group selected from

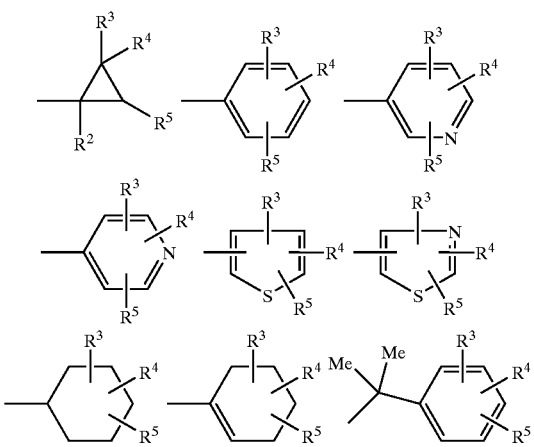

In general, such compounds are prepared in accordance with the following scheme II:

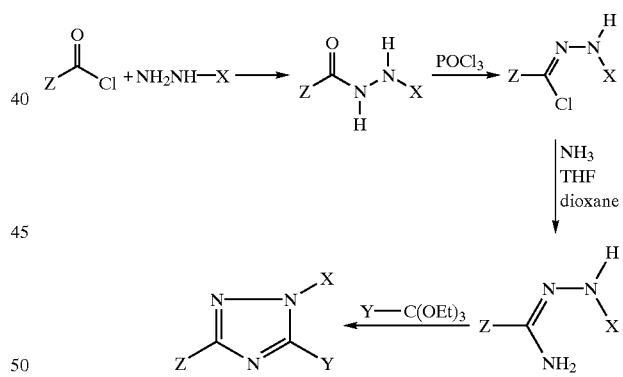

Typical reaction conditions are illustrated in Examples 16–19.

EXAMPLE 16

3,5-Dichloropyrdine-4-carboxylic acid, 4-chlorophenylhydrazide

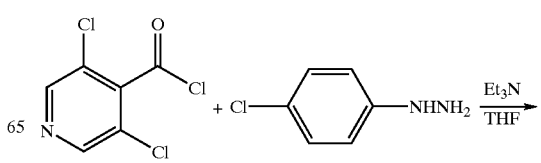

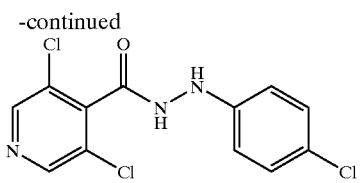

Triethylamine (1.40 mL, 1.02 g, 10.1 mmol) was added to a suspension of 4-chlorophenylhydrazine hydrochloride (1.83 g, 98%, 10.0 mmol) in THF (75 mL). The mixture was stirred under nitrogen at room temperature for 2.75 h. More triethylamine (3.0 mL, 21.6 mmol) was added followed by dropwise addition of a solution of freshly-prepared 3,5-dichloropyridine-4-carbonyl chloride (10.0 mmol) in THF (20 mL). After stirring overnight, the reaction mixture was concentrated under reduced pressure. The residue was partitioned between ethyl acetate (100 mL) and water (50 mL). The layers were shaken together and allowed to separate. The organic phase was dried ($Na_2SO_4$) and concentrated, leaving 3.04 g of a tan solid, mp 201–203.5° C. Recrystallized from ethyl acetate/cyclohexane and then from ethanol furnished crystals which melted at 206–207.5° C.

Anal. Calcd for $C_{12}H_8Cl_3N_3O$: C, 45.53; H, 2.55; N, 13.27. Found: C, 45.59; H, 2.49; N, 13.15.

$^1$H NMR ($CDCl_3$, 300 MHz) δ6.80–7.24 (m, 4H), 8.40–8.56 (m, 2H); IR (nujol) $v_{max}$ 3141, 1660 cm$^{-1}$; MS: m/e 315 (M$^+$).

EXAMPLE 17

3,5-Dichloropyridine-4-carbonyl chloride, 4-chlorophenylhydrazone

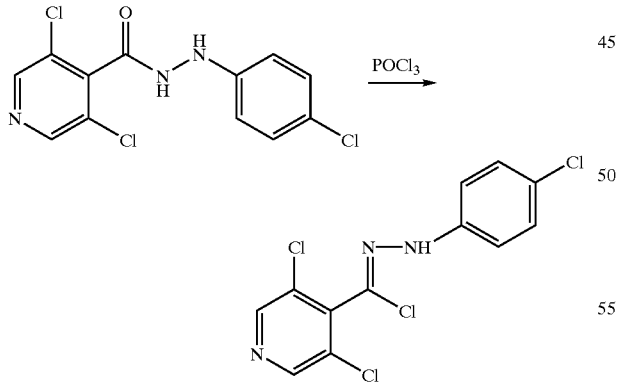

A mixture of 3,5-dichloropyrdine-4-carboxylic acid, 4-chlorophenylhydrazide (1.50 g, 4.74 mmol) and phosphorus oxychloride (10 mL) containing two drops of DMF was stirred at reflux for 2 h. The clear solution was cooled, concentrated in vacuo, and the resulting heavy oil was used without further purification.

EXAMPLE 18

N$^1$-(4-Chlorophenyl)-3,5-dichloro-4-pyridylcarboxamidrazone

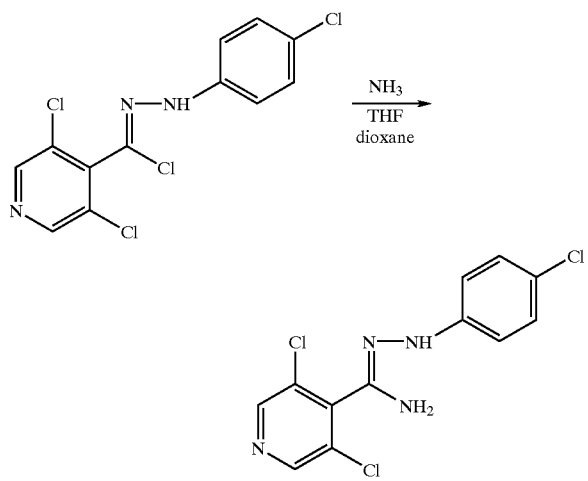

To a solution of 3,5-dichloropyridine-4-carbonyl chloride, 4-chlorophenylhydrazone in THF (40 mL) stirred under nitrogen at −50° C. was added dropwise a solution of ammonia in dioxane (34.5 mL, 0.5 M, 17.2 mmol). During the addition, the temperature rose to 0° C. When the addition was complete, the mixture was stirred 15 min and then concentrated under reduced pressure. The residue was used without further purification.

EXAMPLE 19

1-(4-Chlorophenyl)-5-methyl-3-(3,5-dichloro-4-pyridyl)-1H-1,2,4-triazole

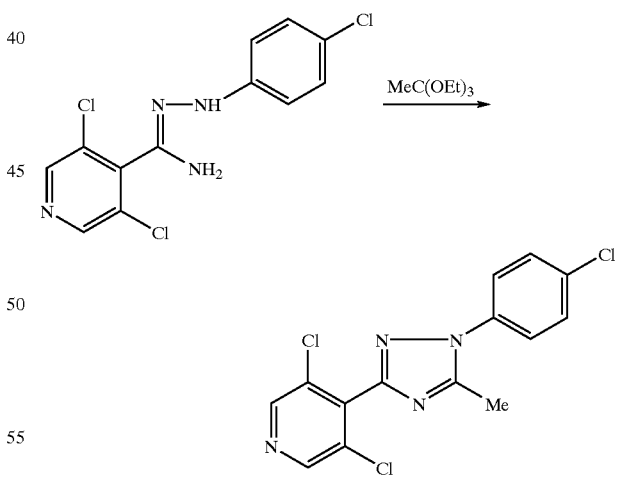

N$^1$-(4-Chlorophenyl)-3,5-dichloro-4-pyridyl carboxamidrazone was stirred at reflux in triethyl orthoacetate (15 mL) for 4 h. The reaction mixture was evaporated under reduced pressure and the residue was partitioned between ether and water. The layers were shaken together, separated, and the aqueous phase was extracted with ether. The combined ether layers were dried ($Na_2SO_4$) and evaporated under reduced pressure. The residue was triturated with ether and filtered. Concentration of the filtrate left a pasty solid, which was chromatographed on silica, eluting with 20% ether in hexane. The ether percentage was increased to 27% in two increments. Evaporation of appropriate fractions gave 180 mg of the triazole, mp 139–144° C. A sample from a separate lot melted at 142–145° C. following recrystallization from cyclohexane.

$^1$H NMR (CDCl$_3$, 300 MHz) δ8.64 (s, 2H), 7.54 (m, 4H), 2.66 (s, 3H); MS: m/e 338 (M$^+$).

Anal. Calcd for $C_{14}H_9Cl_3N_4$: C, 49.51; H, 2.67; N, 16.50. Found: C, 49.62; H, 2.61; N, 16.39.

Phytologically acceptable acid addition salts of the compounds of formula (1) are also within the scope of the invention. For example, boron tetrafluoride, hydrogen chloride, hydrogen bromide, hydrogen iodide, hydrogen sulfate, or organic acid salts may be used.

The compounds identified in the following Tables 1–3 were prepared using the procedures illustrated in the foregoing examples, and the compounds were tested against cotton aphid, two-spotted spider mite and sweetpotato whitefly using procedures described hereinafter.

TABLE 1

| Cmpd No. | R$^7$ | R$^8$ | X | Y | mp ° C. | CA† | TSSM‡ | WF* |
|---|---|---|---|---|---|---|---|---|
| 1 | Cl | Cl | CH$_3$ | 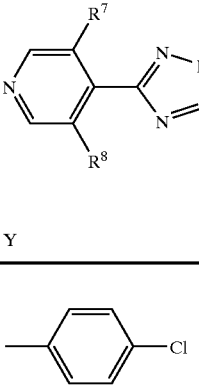 | 130–135 | A | A | A |
| 2 | Cl | Cl | CH$_3$ | 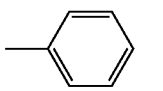 | oil | B | A | F |
| 3 | Cl | Cl | CH$_3$ | 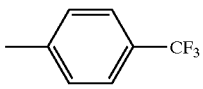 | 81–83 | B | A | A |
| 4 | Cl | Cl | CH$_3$ | 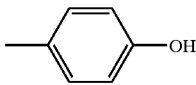 | 251–252 | E | B | F |
| 5 | Cl | Cl | CH$_3$ | 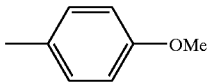 | oil | C | A | F |
| 6 | Cl | Cl | CH$_3$ | 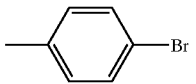 | 110–112 | B | A | A |
| 7 | Cl | Cl | CH$_3$ | 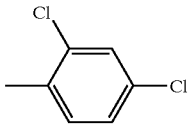 | 79–81 | B | A | A |
| 8 | Cl | Cl | CH$_3$ | 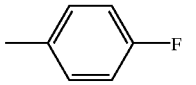 | 123–126 | B | A | C |
| 9 | Cl | Cl | CH$_3$ | 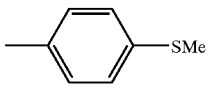 | oil | B | A | G |

TABLE 1-continued
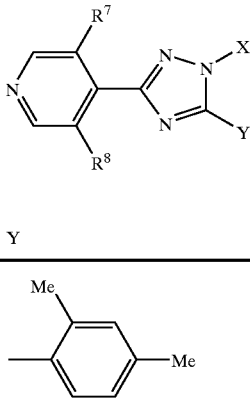
| Cmpd No. | R⁷ | R⁸ | X | Y | mp ° C. | CA† | TSSM‡ | WF* |
|---|---|---|---|---|---|---|---|---|
| 10 | Cl | Cl | CH₃ | 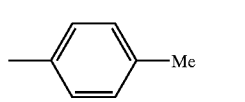 | oil | C | A | D |
| 11 | Cl | Cl | CH₃ | 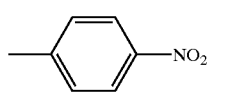 | oil | B | A | D |
| 12 | Cl | Cl | CH₃ | 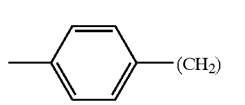 | 162–163 | C | A | C |
| 13 | Cl | Cl | CH₃ | 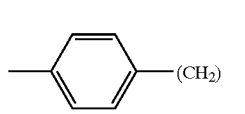 | oil | B | A | F |
| 14 | Cl | Cl | CH₃ | 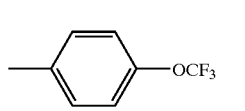 | oil | C | A | F |
| 15 | Cl | Cl | CH₃ | 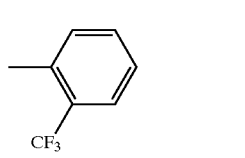 | Oil | B | A | A |
| 16 | Cl | Cl | CH₃ | 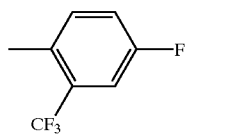 | Oil | B | A | B |
| 17 | Cl | Cl | CH₃ | 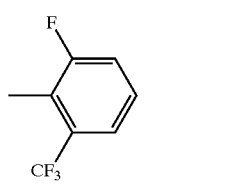 | Oil | E | A | B |
| 18 | Cl | Cl | CH₃ | 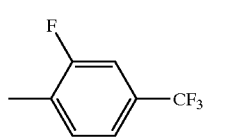 | 124–126 | F | F | G |
| 19 | Cl | Cl | CH₃ |  | Oil | B | | F |

TABLE 1-continued

| Cmpd No. | R7 | R8 | X | Y | mp °C. | CA† | TSSM‡ | WF* |
|---|---|---|---|---|---|---|---|---|
| 20 | Cl | Cl | CH3 | 4-OCF2-phenyl | 70–77 | A | A | B |
| 21 | Cl | Cl | CH3 | 2-F,4-Cl-phenyl | 110–116 | A | A | C |
| 22 | Cl | Cl | CH3 | 3,4-diCl-phenyl | Oil | A | A | A |
| 23 | Cl | F | CH3 | 4-Cl-phenyl | Oil | A | A | D |
| 24 | Cl | Cl | CH3 | 2-NO2,4-NO2-phenyl | 65–70 | B | B | C |
| 25 | Cl | OMe | CH3 | 4-Br-phenyl | Oil | B |  | F |
| 26 | Cl | Cl | CH3 | 2-Cl-phenyl | Oil | A | A | A |
| 27 | Cl | Cl | CH3 | 2-Br-phenyl | Oil | B | A | A |
| 28 | Cl | Cl | CH3 | 3,4-diF-phenyl | Oil | A | A | A |
| 29 | Cl | Cl | CH3 | 3-CF3-phenyl | Oil | A | A | F |

TABLE 1-continued
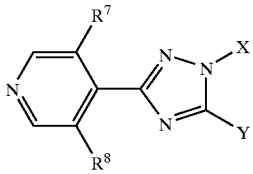
| Cmpd No. | R⁷ | R⁸ | X | Y | mp °C. | CA† | TSSM‡ | WF* |
|---|---|---|---|---|---|---|---|---|
| 30 | Cl | Cl | CH₃ | 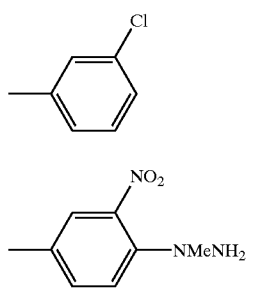 3-Cl-phenyl | Oil | B | A | E |
| 31 | Cl | Cl | CH₃ | 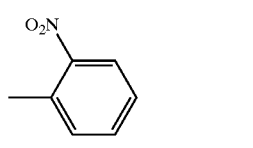 2-NO₂-4-NMeNH₂-phenyl | Oil | F | D | G |
| 32 | Cl | Cl | CH₃ | 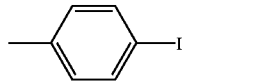 2-NO₂-phenyl | Oil | C | A | F |
| 33 | Cl | Cl | CH₃ | 4-I-phenyl | Oil | B | A | A |
| 34 | Cl | Cl | CH₃ | 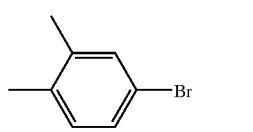 4-Br-2-Me-phenyl | 97–100 | A | A | F |
| 35 | Cl | Cl | CH₃ | 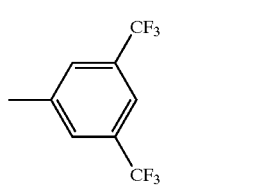 3,5-(CF₃)₂-phenyl | 95–97 | C | F | F |
| 36 | Cl | Cl | CH₃ | 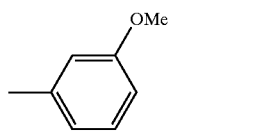 3-OMe-phenyl | Oil | B | A | F |
| 37 | Cl | Cl | CH₃ | 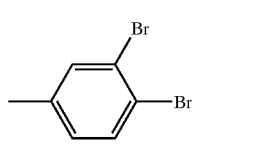 3,4-Br₂-phenyl | Oil | A | A | F |
| 38 | Cl | Cl | CH₃ | 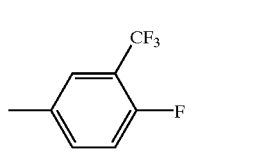 4-F-3-CF₃-phenyl | Oil | A | A | F |

TABLE 1-continued

[Structure: pyridine with R7, R8 substituents, connected to triazole ring with N-X and Y groups]

| Cmpd No. | R7 | R8 | X | Y | mp °C. | CA† | TSSM‡ | WF* |
|---|---|---|---|---|---|---|---|---|
| 39 | Cl | Cl | H | 4-CF₃-phenyl | 194–197 | G | A | F |
| 40 | Cl | Cl | CH₃ | 3-Me-phenyl | Oil | B | G | F |
| 41 | Cl | Cl | CH₃ | 2-Me-phenyl | Oil | A | G | F |
| 42 | Cl | Cl | CH₃ | 3-F-phenyl | Oil | A | G | F |
| 43 | Cl | Cl | CH₃ | 4-CN-phenyl | Oil | B | A | E |
| 44 | Cl | Cl | CH₃ | 3-Br-phenyl | Oil | A | A | F |
| 45 | Cl | SMe | CH₃ | 4-Br-phenyl | 126–128 | B | B | F |
| 46 | Cl | SMe | CH₃ | 4-SMe-phenyl | Oil | A |  | E |
| 47 | Cl | SMe | CH₃ | 4-CF₃-phenyl | Oil | C | F | E |
| 48 | Cl | H | CH₃ | 4-Cl-phenyl | 117–120 | B | G | C |
| 49 | Cl | Cl | CH₃ | 2-Me-6-Br-phenyl | 67–70 | A | A | B |

TABLE 1-continued

| Cmpd No. | R⁷ | R⁸ | X | Y | mp °C. | CA† | TSSM‡ | WF* |
|---|---|---|---|---|---|---|---|---|
| 50 | Cl | Cl | CH₃ | 2-fluorophenyl | Oil | B | A | F |
| 51 | Cl | Cl | CH₃ | 3,5-dichlorophenyl | 110–113 | B | A | C |
| 52 | Cl | Cl | CH₃ | 3-fluoro-5-trifluoromethylphenyl | Oil | B | A | F |
| 53 | Cl | Cl | Et | 4-bromophenyl | 123–125 | B | A | F |
| 54 | Cl | Cl | H | 4-bromophenyl | 183–185 | G | G | F |
| 55 | Cl | Cl | n-pentyl | 4-bromophenyl | Oil | F | C | F |
| 56 | Cl | Cl | CH₃ | 3,4,5-trifluorophenyl | Oil | B | A | E |
| 57 | Cl | Cl | CH₃ | 3,5-difluorophenyl | Oil | B | A | E |
| 58 | Cl | Cl | CH₃ | 4-(trifluoromethylthio)phenyl | Oil | A | A | D |

TABLE 1-continued

| Cmpd No. | R⁷ | R⁸ | X | Y | mp °C. | CA† | TSSM‡ | WF* |
|---|---|---|---|---|---|---|---|---|
| 59 | SMe | SMe | CH₃ | 4-CF₃-phenyl | 134–137 | F | F | F |
| 60 | Cl | SOMe | CH₃ | 4-CF₃-phenyl | 182–183 | F | A | F |
| 61 | Cl | Me | CH₃ | 4-CF₃-phenyl | Oil | A | A | F |
| 62 | Cl | Cl | CH₃ | 2-CF₃-4-Cl-phenyl | Oil | B | A | F |
| 63 | Cl | Cl | CH₃ | 3-F-4-CF₃-phenyl | Oil | A | A | F |
| 64 | Cl | Cl | CH₃ | 3-CF₃-5-NO₂-phenyl | 113–118 | F | G | F |
| 65 | Cl | Cl | CH₃ | 3-CF₃-5-NH₂-phenyl | 201–203 | F | G | F |
| 66 | Cl | Cl | CH₃ | 3-CF₃-5-NOH-phenyl | 184–186 | F | E | F |
| 67 | Cl | Cl | Cyclohexyl | 4-Br-phenyl | 137–139 | F | G | F |

TABLE 1-continued
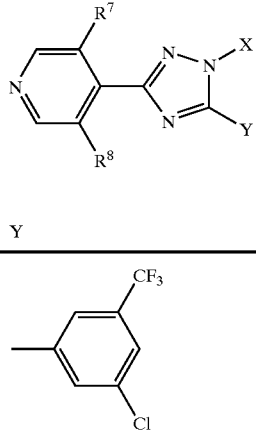
| Cmpd No. | R⁷ | R⁸ | X | Y | mp °C. | CA† | TSSM‡ | WF* |
|---|---|---|---|---|---|---|---|---|
| 68 | Cl | Cl | CH₃ | 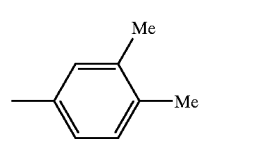 3-CF₃, 5-Cl phenyl | 103–106 | B | F | B |
| 69 | Cl | Cl | CH₃ | 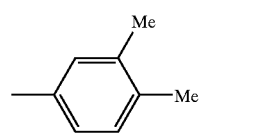 2,3-diMe phenyl | 83–85 | E | A | F |
| 70 | Cl | Cl | H | 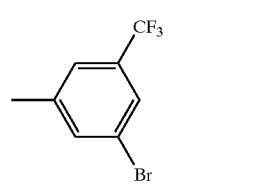 2,3-diMe phenyl | 236–238 | F | F | F |
| 71 | Cl | Cl | CH₃ | 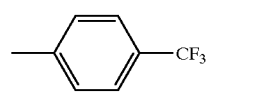 3-CF₃, 5-Br phenyl | 120–122 | A | F | A |
| 72 | F | F | CH₃ | 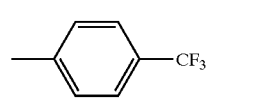 4-CF₃ phenyl | 82–85 | B | | E |
| 73 | Cl | F | CH₃ | 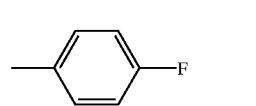 4-CF₃ phenyl | Oil | A | A | F |
| 74 | F | F | CH₃ | 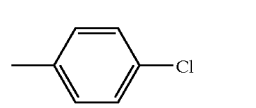 4-F phenyl | 114–115 | B | A | B |
| 75 | F | F | CH₃ | 4-Cl phenyl | | A | | F |
| 76 | Cl | F | CH₃ | 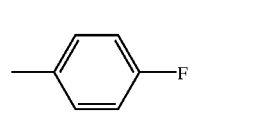 4-F phenyl | 74–75 | A | | D |
| 77 | Cl | Cl | H | 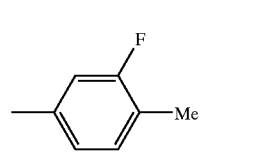 3-F, 4-Me phenyl | Oil | G | B | F |

TABLE 1-continued

| Cmpd No. | R⁷ | R⁸ | X | Y | mp °C. | CA† | TSSM‡ | WF* |
|---|---|---|---|---|---|---|---|---|
| 78 | Cl | Cl | CH₃ | 2-methyl-4-fluorophenyl (F, Me substituted phenyl) | Oil | A | A | F |
| 79 | Cl | Cl | CH₃ | 3-methyl-4-chlorophenyl | 111–114 | A | A | F |
| 80 | Cl | Cl | CH₃ | 3-(trifluoromethoxy)phenyl | Oil | A | A | A |
| 81 | Cl | Cl | CH₃ | 3-methyl-4-bromophenyl | Oil | A | A | F |
| 82 | Cl | Cl | CH₃ | 3-chloro-4-fluorophenyl | Oil | B | A | A |
| 83 | Cl | Cl | CH₃ | biphenyl-4-yl | 166–168 | A | A | F |
| 84 | Cl | Cl | CH₃ | 4-(pyridin-4-yl)phenyl | 101–104 | C | A | G |
| 85 | Cl | Cl | CH₃ | 4-[(3-chloro-5-trifluoromethylpyridin-2-yl)oxy]phenyl | oil | B | B | G |
| 86 | Cl | Cl | CH₃ | 2,3,5-trichlorothiophen-4-yl | 135–137 | C | A | F |
| 87 | Cl | Cl | CH₃ | thiophen-2-yl | oil | C | A | F |

TABLE 1-continued
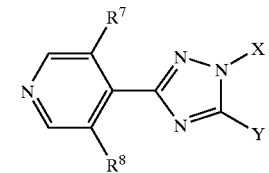
| Cmpd No. | R⁷ | R⁸ | X | Y | mp °C. | CA† | TSSM‡ | WF* |
|---|---|---|---|---|---|---|---|---|
| 88 | Cl | Cl | CH₃ | 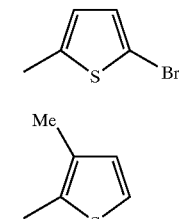 | 143–148 | A | A | B |
| 89 | Cl | Cl | CH₃ | 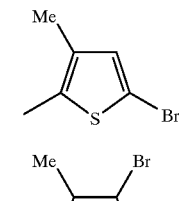 | oil | E | A | F |
| 90 | Cl | Cl | CH₃ | 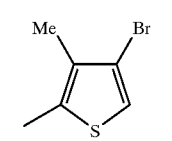 | oil | D | A | F |
| 91 | Cl | Cl | CH₃ | 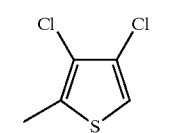 | 114–115 | C | A | F |
| 92 | Cl | Cl | CH₃ | 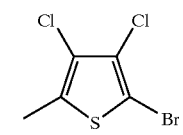 | 101–102 | D | A | F |
| 93 | Cl | Cl | CH₃ | 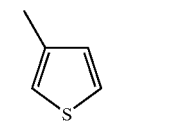 | Oil | A | A | F |
| 94 | Cl | Cl | CH₃ | 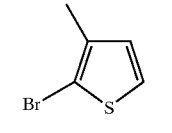 | 120–121 | F | G | F |
| 95 | Cl | Cl | CH₃ | 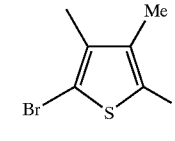 | 115–120 | C | A | F |
| 96 | Cl | Cl | CH₃ | 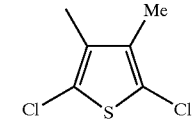 | oil | C | | |
| 97 | Cl | Cl | CH₃ |  | Oil | E | | |

TABLE 1-continued

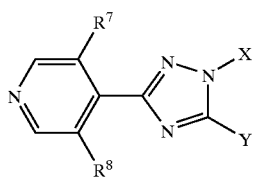

| Cmpd No. | R⁷ | R⁸ | X | Y | mp °C. | CA† | TSSM‡ | WF* |
|---|---|---|---|---|---|---|---|---|
| 98 | Cl | Cl | CH₃ | 4-Me-thiophen-3-yl (Me) | 100–102 | E | A | F |
| 99 | Cl | Cl | CH₃ | 5-Cl-3-Me-thiophen-2-yl | Oil | B | A | F |
| 100 | Cl | Cl | CH₃ | 5-Cl-4-Me-thiophen-2-yl | Oil | B | | B |
| 101 | Cl | Cl | CH₃ | 2,5-diCl-3-Me-thiophen-4-yl | Oil | C | A | F |
| 102 | Cl | Cl | CH₃ | 2,3,5-triBr-4-Me-thiophen | Oil | F | A | F |
| 103 | Cl | Cl | CH₃ | 5-Br-4-Me-thiophen-2-yl | Oil | A | A | F |
| 104 | Cl | Cl | CH₃ | 2,5-diBr-4-Me-thiophen | Oil | D | F | F |
| 105 | Cl | Cl | CH₃ | 5-Me-2-(OCH₂CF₃)-pyridin-? | oil | B | A | F |
| 106 | Cl | Cl | CH₃ | 5-Me-2-OMe-pyridin-? | oil | B | A | F |
| 107 | Cl | Cl | CH₃ | 5-Me-2-NMeNH₂-pyridin-? | oil | F | G | G |

TABLE 1-continued

| Cmpd No. | R⁷ | R⁸ | X | Y | mp ° C. | CA† | TSSM‡ | WF* |
|---|---|---|---|---|---|---|---|---|
| 108 | Cl | Cl | CH₃ | 5-(3-chlorophenoxy)pyridin-2-yl | oil | C | A | G |
| 109 | Cl | Cl | CH₃ | pyridin-3-yl | 106–116 | D | A | G |
| 110 | Cl | Cl | CH₃ | 6-chloropyridin-3-yl |  | A | A | D |
| 111 | Cl | Cl | CH₃ | pyridin-3-yl N-oxide |  | D | E | F |
| 112 | Cl | Cl | CH₃ | 2,6-dichloropyridin-4-yl | 162–164 | B | E | E |
| 113 | Cl | Cl | CH₃ | pyridin-4-yl | 130–132 | C | A | F |
| 114 | Cl | Cl | CH₃ | 5-chloropyridin-2-yl | 106–107 | A | A | F |
| 115 | Cl | Cl | CH₃ | 5-bromopyridin-3-yl | 140–144 | A | A | F |
| 116 | Cl | Cl | CH₃ | 6-(trifluoromethyl)pyridin-3-yl | 117–120 | A | A | F |
| 117 | Cl | Cl | CH₃ | 5-chloropyridin-3-yl | Oil | A | A | E |

TABLE 1-continued

[Structure: pyridine with R7, R8 substituents connected to triazole with X, Y substituents]

| Cmpd No. | R⁷ | R⁸ | X | Y | mp °C. | CA† | TSSM‡ | WF* |
|---|---|---|---|---|---|---|---|---|
| 118 | Cl | Cl | CH₃ | 5-CF₃-pyridin-2-yl | Oil | B | A | F |
| 119 | Cl | Cl | CH₃ | 3,6-dichloropyridin-... | 129–135 | B | A | F |
| 120 | Cl | Cl | CH₃ | 5-Me-pyridin-2-yl | 126–128 | F | A | F |
| 121 | Cl | Cl | CH₃ | 6-SMe-pyridin-3-yl | 121–123 |  | B | F |
| 122 | Cl | Cl | CH₃ | 6-SO₂Me-pyridin-3-yl | 183–186 | F | G | G |
| 123 | Cl | Cl | CH₃ | 6-NHCO₂t-butyl-pyridin-3-yl | Oil | G | A | F |
| 124 | Cl | Cl | H | 6-SMe-pyridin-3-yl | 198–200 | G |  | F |
| 125 | Cl | Cl | CH₃ | 6-SOMe-pyridin-3-yl | Oil | F |  | E |
| 126 | Cl | Cl | CH₃ | 6-Cl-pyridin-3-yl (with Me) | Oil | B | A | B |
| 127 | Cl | Cl | CH₃ | 4,5-dimethyl-2-(4-chlorophenyl)thiazol-... | 185–187 | F | A | F |

TABLE 1-continued

| Cmpd No. | R⁷ | R⁸ | X | Y | mp °C. | CA† | TSSM‡ | WF* |
|---|---|---|---|---|---|---|---|---|
| 128 | Cl | Cl | CH₃ | 4,5-dimethyl-2-(trifluoromethyl)thiazole | 136–138 | A | A | F |
| 129 | Cl | Cl | CH₃ | 4-bromo-5-methyl-3-[3-(trifluoromethyl)phenyl]isothiazole | 56–59 | A | A | F |
| 130 | Cl | Cl | CH₃ | 4-bromo-5-methyl-3-(2,4-dichlorophenyl)isothiazole | 127–129 | B | D | F |
| 131 | Cl | Cl | CH₃ | 4,5-dimethylthiazole | 143–145 | B | A | F |
| 132 | Cl | Cl | CH₃ | 4,5-dimethylisothiazole | 82–84 | F | F | F |
| 133 | Cl | Cl | CH₃ | 2,2-dichloro-1-methylcyclopropyl | 79–83 | E | A | A |
| 134 | Cl | Cl | 4-chlorophenyl | 2,2-dichloro-1-methylcyclopropyl | 117–119 | G | A | F |
| 135 | Cl | Cl | 4-(trifluoromethyl)phenyl | 2,2-dichloro-1-methylcyclopropyl | 158–160 | F | A | F |

TABLE 1-continued

[Structure: pyridine with R7, R8 substituents, connected to triazole with N-X and Y groups]

| Cmpd No. | R⁷ | R⁸ | X | Y | mp °C. | CA† | TSSM‡ | WF* |
|---|---|---|---|---|---|---|---|---|
| 136 | Cl | Cl | 4-bromobenzyl | 1,1-dichloro-2-methylcyclopropyl | 138–148 | G | B | D |
| 137 | Cl | Cl | cyclohexylmethyl | 1,1-dichloro-2-methylcyclopropyl | 139–142 | F | G | F |
| 138 | Cl | Cl |  | Me on 4-chlorobenzyl (4-Cl-C₆H₄-CH(Me)-) | 144–146 | B | A | A |
| 139 | Cl | Cl |  | Me on 4-CF₃-benzyl (4-CF₃-C₆H₄-CH(Me)-) | Oil | C | A | A |
| 140 | Cl | Cl | CH₃ | 2-(4-chlorophenyl)prop-2-yl | oil | F | A | F |
| 141 | Cl | Cl | CH₃ | 2-(4-trifluoromethylphenyl)prop-2-yl | 96–101 | D | A | E |
| 142 | Cl | Cl | CH₃ | 2-(3-trifluoromethylphenyl)prop-2-yl | 98½–100 | F | A | F |
| 143 | Cl | Cl | CH₃ | 1-(4-trifluoromethylphenyl)ethyl | Oil | B |  | F |
| 144 | Cl | Cl | CH₃ | cyclohexyl | Oil | C | A | F |
| 145 | Cl | Cl | CH₃ | 2-chlorocyclohex-1-enyl | 117–121 | E | A | D |
| 146 | Cl | Cl | CH₃ | quinolin-3-yl | 160–164 | B | A | E |

TABLE 2

(Structure: pyridine with X1-X5 substituents linked to triazole with X substituent and 4-chlorophenyl group)

| cmpd no. | X1 | X2 | X3 | X4 | X5 | X | mp | CA† | TSSM‡ | WF* |
|---|---|---|---|---|---|---|---|---|---|---|
| 148 | Cl | Cl | Cl | Cl |  | Me | 129–134 | F |  |  |
| 149 | Cl | Cl | H | H | O | Me | 161–166 | A | A | D |
| 150 | F | F | F | F |  | Me | oil | F | G | F |
| 151 | Cl | Cl | H | H | O | Me | 151–153 | A | A | A |
| 152 | Cl | Cl | H | H | O | Me | 169–173 |  |  | B |
| 153 | Cl | H | Cl | H |  | Me | 133–134 | B | G | F |
| 154 | Cl | H | F | F |  | Me | Oil | D | G | D |

TABLE 3

(Structure: pyridine with X1-X3 and triazole linked to phenyl with X4, X5 substituents and R group)

| cmpd no. | X1 | X2 | X3 | X4 | X5 | R | mp | CA† | TSSM‡ | WF* |
|---|---|---|---|---|---|---|---|---|---|---|
| 155 | F | F | F | F | Cl | Me | 154–156 | G |  |  |
| 156 | Cl | H | H | Cl | Cl | Me | 98–102 | G | F |  |
| 157 | H | H | H | Cl | Cl | Me | oil | B | F | G |
| 158 | H | Cl | H | Cl | Cl | Me | 105–107 | F | G | F |
| 159 | H | H | H | Cl | Me | Me | 113–117 | F |  | F |
| 160 | H | H | H | Cl | CF3 | Me | oil | B | A | G |

TABLE 4

(Structure: pyridine with X1-X3 linked to triazole with R and phenyl bearing X4, X5)

| cmpd no. | X1 | X2 | X3 | X4 | X5 | R | mp | CA† | TSSM‡ | WF* |
|---|---|---|---|---|---|---|---|---|---|---|
| 161 | Cl | H | H | H | Cl | Me | 176–177 | F |  |  |
| 162 | Cl | H | H | Cl | Cl | Me | oil | A | G |  |
| 163 | Cl | Cl | H | CF3 | Cl | Me | 124–126 | G | G | F |

CA† refers to activity at 50 ppm against cotton aphid,
TSSM‡ refers to activity at 100 ppm against two-spotted spider mite, and
In each case the rating scale is as follows

| % Control | Rating |
|---|---|
| 91–100 | A |
| 81–90 | B |
| 71–80 | C |
| 61–70 | D |
| 51–60 | E |
| less than 51 | F |
| inactive | G |

Insecticide and Miticide Utility

The compounds of the formulae (1) are suitable for controlling pests on animals and plants. Such pests belong mainly to the arthropod family, such as, especially, insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera, and arachnids of the order Acarina, such as, for example, mites, aphids, and ticks.

Therefore, the present invention also is directed to a method for inhibiting an insect, mite, or aphid which comprises applying to a locus of the insect or mite an insect- or mite-inhibiting amount of a compound of formula (1).

The compounds are useful for reducing populations of insects and mites and are useful in a method of inhibiting an insect or mite population which comprises applying to a locus of the insect or mite an effective insect- or mite-inactivating amount of a compound of formula (1). The "locus" of insects or mites is a term used herein to refer to the environment in which the insects or mites live or where their eggs are present, including the air surrounding them, the food they eat, or objects which they contact. For example, plant-ingesting insects or mites can be controlled by applying the active compound to plant parts that the insects or mites eat, particularly the foliage. It is contemplated that the compounds might also be useful to protect textiles, paper, stored grain, or seeds by applying an active compound to such substance. The term "inhibiting an insect or mite" refers to a decrease in the numbers of living insects or mites, or a decrease in the number of viable insect or mite eggs. The extent of reduction accomplished by a compound depends, of course, upon the application rate of the compound, the particular compound used, and the target insect or mite species. At least an inactivating amount should be used. The terms "insect-inactivating amount" and "mite-inactivating amount" are used to describe the amount, which is sufficient to cause a measurable reduction in the treated insect or mite, population. Generally an amount in the range from about 1 to about 1000 ppm active compound is used.

In a preferred embodiment, the present invention is directed to a method for inhibiting a mite or aphid which comprises applying to a plant an effective mite- or aphid-inactivating amount of a compound of formula (1).

Insecticidal Test for Cotton Aphid (*Aphis gossypii*)

To prepare spray solutions, 1 mg of each test compound was dissolved into 1 mL of a 90:10 acetone:ethanol solvent. This 1 mL of chemical solution was added to 19 mL of water containing 0.05% Tween 20 surfactant to produce a 50 ppm spray solution.

Squash cotyledons were infested with cotton aphid (all life stages) 16–20 hours prior to application of spray solution. The solution was sprayed on both sides of each infested squash cotyledon (0.5 mL×2 each side) with a sweeping action until runoff. The plants were allowed to air dry and held for 3 days in a controlled room at 26° C. and 40% relative humidity after which time the test was graded. Grading was by actual count using a dissecting microscope and comparison of test counts to the untreated check. Results are given in Tables 1–3 as percent control based on population reduction versus the untreated.

Insecticidal Test for Two-spotted Spider Mite (*Tetranychus urticae*)
Ovicide Method Ten adult female two-spotted spider mites were placed on eight 2.2 cm leaf discs of cotton leaf, allowed to oviposit over 24 hours, and thereafter removed. The leaf discs were sprayed with 100 ppm test solutions using a hand syringe, then allowed to dry with sixteen discs left untreated as a negative control. Discs were placed on an agar substrate and held at 24° C. and 90% relative humidity for 6 days. Percent control based on the number of hatched larvae on treated discs and the number on untreated discs is reported in Tables 1–2.

Evaluation of Tests Compounds on Sweetpotato Whitefly (*Bemisia tabacia*) Under Laboratory Conditions Four mg of each test compound was dissolved by adding 4 ml of a 90:10 acetone:ethanol solvent mixture to the vial containing the sample compound. This solution was added to 16 ml of water containing 0.05% Tween 20 surfactant to produce 20 ml of an 200 ppm spray solution.

Five-week-old cotton plants reared in a greenhouse were stripped of all foliage except for the two uppermost true leaves that were greater than 5 cm in diameter. These plants were then placed into a laboratory colony of whiteflies for two days for oviposition by the colony females. All whiteflies were then removed from the test plants with pressurized air. The spray solution was then applied to the test plants with a hand-held syringe fitted with hollow cone nozzle. One mL spray solution was applied to each leaf top and bottom for a total of 4 mL per plant. Four replications of each test compound utilized a total of 16 mL spray solution. Plants were air dried and then placed in a holding chamber (28° C. and 60% RH) for 13 days. Compound efficacy was evaluated by counting, under an illuminated magnifying glass, the number of large nymphs (3rd–4th instar) per leaf. Percent control based on reduction of large nymphs of a test compound compared to solution-only (no test compound) sprayed plants is reported in Tables 1–3.

Compounds of the invention have demonstrated unexpectedly good activity against citrus red mite, and have also demonstrated unique female sterilization activity against mites, when tested in the following methods:

Citrus Red Mite Ovicide

Ten adult female citrus red mites *Panonychus citri* were placed on six 2 cm leaf discs of orange leaf maintained on an agar substrate. They were allowed to oviposit over 24 hours and then removed by aspiration. The leaf discs were sprayed with test solutions using a hand syringe using a TN-3 nozzle just to wetting, then allowed to dry. Twelve discs were treated with water as a negative control. Discs were maintained on an agar substrate and held at 27 degrees C. and 90% relative humidity for 6 days. Ovicidal activity was calculated by comparing the number of hatched larvae on treated discs with the number on water only treated discs.

Two-spotted Spider Mite Female Sterilization

Adult female two-spotted spider mites *Tetranychus urticae* were sprayed to runoff using the appropriate test solution and allowed to dry. Ten treated females were placed on each of twenty five untreated 2 cm leaf discs of kidney bean. These mites were allowed to oviposit for the selected time interval and then were transferred to new untreated leaf discs. This transfer usually occurred at 24, 48, 72, and 144 hours. Twenty five discs infested with untreated female mites was maintained as a negative control. Discs were held at 27 degrees C. and 90% relative humidity for 6 days. Residual tests were assayed over time by infesting the treated plants with female mites over several time intervals. Female mites were exposed to the treated plants for 16 hours and then transferred to untreated discs as above. Ovicidal activity was calculated by comparing the number of hatched larvae from eggs laid by treated females versus untreated females.

Compounds of the invention have shown activity against Lygus, milkweed bug, plant hoppers, and tobacco bud worm.

In addition to being effective against mites, aphids, and insects when applied to foliage, compounds of formula (1) have systemic activity. Accordingly, another aspect of the invention is a method of protecting a plant from insects which comprises treating plant seed prior to planting it, treating soil where plant seed is to be planted, or treating soil at the roots of a plant after it is planted, with an effective amount of a compound of formula (1).

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects, mites, and aphids is not critical and can readily be determined by those skilled in the art in view of the examples above. In general, concentrations of from-10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 5–20 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species provides exemplification of the wide range of settings in which the present compounds can be used.

Because of the unique ability of mite eggs to resist toxicant action, repeated applications may be desirable to control newly emerged larvae, as is true of other known acaricides.

The following formulations of compounds of the invention are typical of compositions useful in the practice of the present invention.

| A. 0.75 Emulsifiable Concentrate | |
|---|---|
| Compound of formula (1) | 9.38% |
| "TOXIMUL D" (nonionic/anionic surfactant blend) | 2.50% |
| "TOXIMUL H" (nonionic/anionic surfactant blend) | 2.50% |
| "EXXON 200" (naphthalenic solvent) | 85.62% |

| B. 1.5 Emulsifiable Concentrate | |
|---|---|
| Compound of formula (1) | 18.50% |
| "TOXIMUL D" | 2.50% |
| "TOXIMUL H" | 2.50% |
| "EXXON 200" | 76.50% |

| C. 1.0 Emulsifiable Concentrate | |
|---|---|
| Compound of formula (1) | 12.5% |
| N-methylpyrrolidone | 25.00% |
| "TOXIMUL D" | 2.50% |
| "TOXIMUL H" | 2.50% |
| "EXXON 200" | 57.50% |

| D. 1.0 Aqueous Suspension | |
|---|---|
| Compound of formula (1) | 12.00% |
| "PLURONIC P-103" (block copolymer of propylene oxide and ethylene oxide, surfactant) | 1.50% |
| "PROXEL GXL" (biocide/preservative) | .05% |
| "AF-100" (silicon based antifoam agent) | .20% |
| "REAX 88B" (lignosulfonate dispersing agent) | 1.00% |
| propylene glycol | 10.00% |
| veegum | .75% |
| xanthan | .25% |
| water | 74.25% |

| E. 1.0 Aqueous Suspension | |
|---|---|
| Compound of formula (1) | 12.50% |
| "MAKON 10" (10 moles ethyleneoxide nonylphenol surfactant) | 1.00% |
| "ZEOSYL 200" (silica) | 1.00% |
| "AF-100" | 0.20% |
| "AGRIWET FR" (surfactant) | 3.00% |
| 2% xanthan hydrate | 10.00% |
| water | 72.30% |

| F. 1.0 Aqueous Suspension | |
|---|---|
| Compound of formula (1) | 12.50% |
| "MAKON 10" | 1.50% |
| "ZEOSYL 200" (silica) | 1.00% |
| "AF-100" | 0.20% |
| "POLYFON H" (lignosulfonate dispersing agent) | 0.20% |
| 2% xanthan hydrate | 10.00% |
| water | 74.60% |

| G. Wettable Powder | |
|---|---|
| Compound of formula (1) | 25.80% |
| "POLYFON H" | 3.50% |
| "SELLOGEN HR" | 5.00% |
| "STEPANOL ME DRY" | 1.00% |
| gum arabic | 0.50% |
| "HISIL 233" | 2.50% |
| Barden clay | 61.70% |

-continued

| H. 1.0 Aqueous Suspension | |
|---|---|
| Compound of formula (1) | 12.40% |
| "TERGITOL 15S-7" | 5.00% |
| "ZEOSYL 200" | 1.0% |
| "AF-1G0" | 0.20% |
| "POLYFON H" | 0.50% |
| 2% xanthan solution | 10.00% |
| tap water | 70.90% |

| I. 1.0 Emulsifiable Concentrate | |
|---|---|
| Compound of formula (1) | 12.40% |
| "TOXIMUL D" | 2.50% |
| "TOXIMUL H" | 2.50% |
| "EXXON 200" | 82.60% |

| J. Wettable Powder | |
|---|---|
| Compound of formula (1) | 25.80% |
| "SELLOGEN HR" | 5.00% |
| "POLYFON H" | 4.00% |
| "STEPANOL ME DRY" | 2.00% |
| "HISIL 233" | 3.00% |
| Barden clay | 60.20% |

| K. 0.5 Emulsifiable Concentrate | |
|---|---|
| Compound of formula (1) | 6.19% |
| "TOXIMUL H" | 3.60% |
| "TOXIMUL D" | 0.40% |
| "EXXON 200" | 89.81% |

| L. Emulsifiable Concentrate | |
|---|---|
| Compound of formula (1) | 5 to 48% |
| surfactant or surfactant blend | 2 to 20% |
| Aromatic Solvent or Mixture | 55 to 75% |

We claim:

1. A compound of the formula (1)

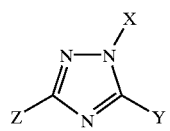

(1)

wherein

Z is a 4-pyridyl group of the formula

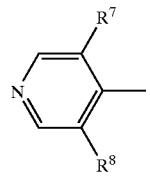

wherein $R^7$ and $R^8$ are independently F or Cl;

one of X and Y is H; $(C_1-C_6)$ alkyl; $(C_1-C_6)$ haloalkyl; $(C_2-C_6)$ alkenyl; $(C_2-C_6)$ alkynyl; $(C_1-C_6)$ alkoxy-substituted $(C_1-C_6)$ alkyl; phenyl; or phenyl substituted with one or more groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyl, benzoyl, $(C_1-C_4)$ alkanoyloxy, $(C_1-C_4)$ alkoxycarbonyl, phenoxycarbonyl, or benzoyloxy;

the other of X and Y is a group selected from

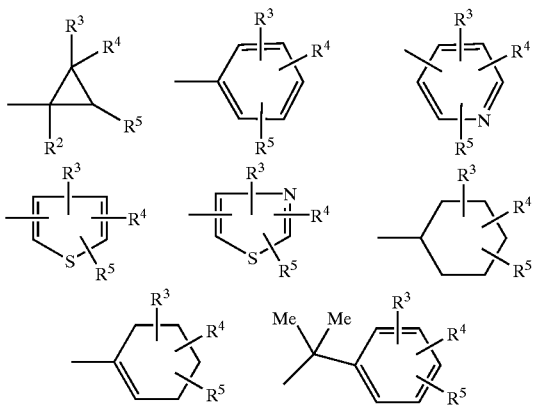

wherein $R^2$ is halo; $(C_1-C_6)$ alkyl; $(C_1-C_6)$ haloalkyl; $(C_2-C_6)$ alkenyl; $(C_2-C_6)$ alkynyl; or $(C_1-C_6)$ alkoxy-substituted $(C_1-C_6)$ alkyl;

$R^3$ is selected from H; halo; $(C_1-C_6)$ alkyl; $(C_7-C_{21})$ straight chain alkyl; hydroxy; $(C_1-C_6)$ alkoxy; $(C_1-C_6)$ haloalkyl; $(C_1-C_6)$ haloalkoxy; $(C_1-C_6)$ alkoxy-substituted $(C_1-C_6)$ alkyl; $(C_1-C_6)$ alkoxy-substituted $(C_1-C_6)$ alkoxy; $(C_1-C_6)$ alkenyl; $(C_2-C_6)$haloalkenyl; CN; $NO_2$; $CO_2R^6$; $CON(R^6)_2$; $(C_3-C_6)$ cycloalkyl; $S(O)_mR^6$; SCN; phenoxy; phenoxy substituted with one or more groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyl, benzoyl, $(C_1-C_4)$ alkanoyloxy, $(C_1-C_4)$ alkoxycarbonyl, phenoxycarbonyl, or benzoyloxy; naphthyl; naphthyl substituted with one or more groups independently selected from halo, halo$(C_1-C_4)$ alkyl, CN, $NO_2$, $(C_1-C_4)$ alkyl, $(C_3-C_4)$ branched alkyl, phenyl, $(C_1-C_4)$ alkoxy, or halo $(C_1-C_4)$ alkoxy; phenyl; phenyl substituted with one or more groups independently selected from halo, $(C_1-C_{10})$ alkyl, branched $(C_3-C_6)$ alkyl, halo $C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyl, benzoyl, $(C_1-C_4)$ alkanoyloxy, $(C_1C_4)$ alkoxycarbonyl, phenoxycarbonyl, or benzoyloxy; $-(CH_2)_nR^6$; $-CH=CHR^6$; $-C\equiv CR^6$; $-CH_2OR^6$; $-CH_2SR^6$; $-CH_2NR^6R^6$; $-OCH_2R^6$; $-SCH_2R^6$; $-NR^6CH_2R^6$; $-NCH_3NH_2$;

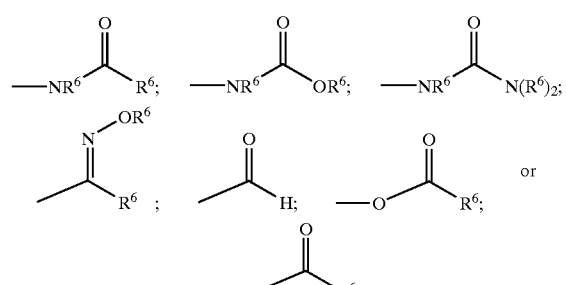

$R^4$ and $R^5$ are independently H; halo; $(C_1-C_6)$ alkyl; $(C_1-C_6)$ alkoxy; $(C_1-C_6)$ haloalkoxy; $(C_1-C_6)$ haloalkoxy; CN; $NO_2$; $CO_2R^6$; $CON(R^6)_2$; or $(C_1-C_6)$ $S(O)_m$ alkyl; or $R^4$ and $R^5$ form a 5 or 6 member saturated or unsaturated carbocyclic ring which may be substituted by 1 or 2 halo, $(C_1-C_6)$ alkyl, $(C_1-C_6)$ alkoxy or $(C_1-C_6)$ haloalkyl groups;

$R^6$ is H; $(C_1-C_6)$ alkyl; $(C_1-C_6)$ haloalkyl; $(C_2-C_6)$ alkenyl; $(C_2-C_6)$ alkynyl; phenyl; or phenyl substituted with one or more groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyl, benzoyl, $(C_1-C_4)$ alkanoyloxy, $(C_1-C_4)$ alkoxycarbonyl, phenoxycarbonyl, or benzoyloxy;

m is 0, 1, or 2; and
n is 1 or 2;

or a phytologically acceptable acid addition salt or N-oxide thereof.

2. A compound of claim 1
wherein

X is $(C_1-C_6)$ alkyl; $(C_1-C_6)$ haloalkyl; $(C_2-C_6)$ alkenyl; $(C_2-C_6)$ alkynyl; or $(C_1-C_6)$ alkoxy-substituted $(C_1-C_6)$ alkyl;

Y is a group selected from

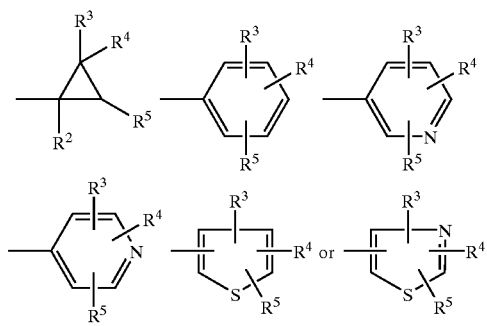

wherein $R^3$ is selected from H; halo ; $(C_1-C_6)$ alkyl; $(C_7-C_{21})$ straight chain alkyl; hydroxy; $(C_1-C_6)$ alkoxy; $(C_1-C_6)$ haloalkyl; $(C_1-C_6)$ haloalkoxy; $(C_1-C_6)$ alkoxy-substituted $(C_1-C_6)$ alkyl; $(C_1-C_6)$ alkoxy-substituted $(C_1-C_6)$ alkoxy; $(C_2-C_6)$ alkenyl; $(C_2-C_6)$ haloalkenyl; CN; $NO_2$; $CO_2R^6$; $CON(R^6)_2$; $(C_3-C_6)$ cycloalkyl; $S(O)_mR^6$; SCN; naphthyl; naphthyl substituted with one or more groups independently selected from halo, halo $(C_1-C_4)$ alkyl, CN, $NO_2$, $(C_1-C_4)$ alkyl, $(C_3-C_4)$ branched alkyl, phenyl, $(C_1-C_4)$ alkoxy, or halo $(C_1-C_4)$ alkoxy; phenyl; phenyl substituted with one or more groups independently selected from halo, $(C_1C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyl, benzoyl, $(C_1-C_4)$ alkanoyloxy, $(C_1-C_4)$ alkoxycarbonyl, phenoxycarbonyl, or benzoyloxy;
$-(CH_2)_nR^6$; $-CH=CHR^6$; $-C\equiv CR^6$; $-CH_2OR^6$; $-CH_2SR^6$; $-CH_2NR^6R^6$; $-OCH_2R^6$; $-SCH_2R^6$; $-NR^6CH_2R^6$;

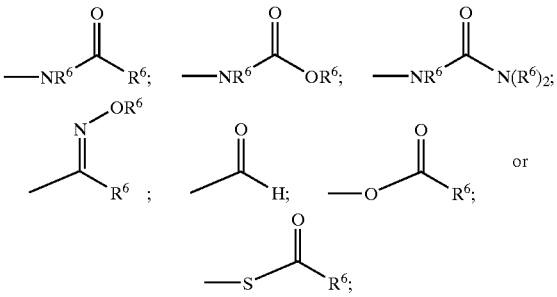

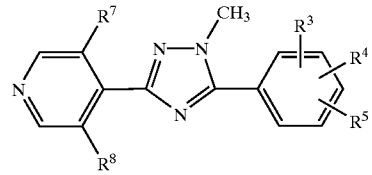

$R^4$ and $R^5$ are independently H; halo; $(C_1-C_6)$ alkyl; $(C_1-C_6)$ alkoxy; $(C_1-C_6)$ haloalkyl; $(C_1-C_6)$ haloalkoxy; CN; $CO_2R^6$; $CON(R^6)_2$; or $(C_1-C_6)$ $S(O)_m$ alkyl; or $R^4$ and $R^5$ form a 5 or 6 member saturated or unsaturated carbocyclic ring which may be substituted by 1 or 2 halo, $(C_1-C_6)$ alkyl, $(C_1-C_6)$ alkoxy or $(C_1-C_6)$ haloalkyl groups.

3. A compound of claim 2 wherein $R^7$ and $R^8$ are both F.
4. A compound of claim 2 wherein $R^7$ and $R^8$ are both Cl.
5. A compound of claim 1 having the formula

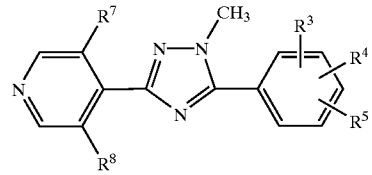

wherein $R^7$ and $R^8$ are independently F or Cl; and $R^3$, $R^4$, and $R^5$ are independently H, Cl, Br, methyl, halomethyl, methoxy, or halomethoxy.

6. A composition for controlling insects or mites which comprises a compound of claim 1 in combination with a phytologically-acceptable carrier.

7. A method of controlling insects or mites which comprises applying to a locus where control is desired an insect- or mite-inactivating amount of a compound of claim 1.

8. The compound of claim 1 which is 3-(3,5-dichloro-4-pyridyl)-5-(4-bromophenyl)-1-methyl-1H-1,2,4-triazole.

9. The compound of claim 1 which is 3-(3,5-dichloro-4-pyridyl)-5-(4-trifluoromethylphenyl)-1-methyl-1H-1,2,4-triazole.

* * * * *

UNITED STATES PATENT AND TRADEMARK OFFICE
CERTIFICATE OF CORRECTION

PATENT NO.    : 6,413,992 B1
DATED         : July 2, 2002
INVENTOR(S)   : Francis E. Tisdell et al.

It is certified that error appears in the above-identified patent and that said Letters Patent is hereby corrected as shown below:

Column 56,
Line 26, should read -- ...alkoxy-substituted ($C_1$-$C_6$) alkoxy; ($C_2$-$C_6$) alk-... -- rather than "...alkoxy-substituted ($C_1$-$C_6$) alkoxy; ($C_1$-$C_6$) alk-..."

Signed and Sealed this

Nineteenth Day of November, 2002

Attest:

Attesting Officer

JAMES E. ROGAN
*Director of the United States Patent and Trademark Office*